(12) United States Patent
Ramurthy et al.

(10) Patent No.: US 7,691,866 B2
(45) Date of Patent: Apr. 6, 2010

(54) 2,6-DISUBSTITUTED QUINAZOLINES, QUINOXALINES, QUINOLINES AND ISOQUINOLINES AND METHODS OF THEIR USE AS INHIBITORS OF RAF KINASE

(75) Inventors: Savithri Ramurthy, Walnut Creek, CA (US); Paul A. Renhowe, Danville, CA (US); Sharadha Subramanian, San Ramon, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 1456 days.

(21) Appl. No.: 10/966,358

(22) Filed: Oct. 15, 2004

(65) Prior Publication Data

US 2005/0085482 A1 Apr. 21, 2005

Related U.S. Application Data

(60) Provisional application No. 60/511,851, filed on Oct. 16, 2003.

(51) Int. Cl.
*C07D 239/84* (2006.01)
*C07D 403/12* (2006.01)
*A61K 31/517* (2006.01)

(52) U.S. Cl. .............. 514/266.21; 544/284; 544/292; 514/266.4

(58) Field of Classification Search ........... 514/266.21, 514/266.4; 544/284, 292
See application file for complete search history.

(56) References Cited

U.S. PATENT DOCUMENTS

| 3,149,113 | A | | 9/1964 | Brown et al. |
| 3,177,218 | A | | 4/1965 | Brown et al. |
| 7,238,698 | B2 | * | 7/2007 | Dunn et al. ............ 514/258.1 |
| 7,456,185 | B2 | * | 11/2008 | Dunn et al. ............ 514/258.1 |
| 2002/0165394 | A1 | | 11/2002 | Dumas et al. |
| 2003/0008866 | A1 | * | 1/2003 | Nuss et al. ............ 514/224.2 |

FOREIGN PATENT DOCUMENTS

| EP | 096214 | 12/1983 |
| EP | 1072263 A1 | 3/1999 |
| WO | WO 02/36570 A1 | 5/2002 |
| WO | WO 02/085857 A2 | 10/2002 |
| WO | WO 03/024448 A2 | 3/2003 |

OTHER PUBLICATIONS

Davis et al., "2,4-Diamino-5-benzylpyrimidines and Analogues as Antibacterial Agents. 11. Quinolylmethyl Analogues with Basic Substituents Conveying Specificity" *J. Med. Chem.* 32:1936-1942, 1989.
Database Beilstein, Jun. 27, 1988, Database Accession No. BRN: 306344 Shimizu at al. 64(10):47, 1944.
Database Beilstein, Feb. 26, 1991, Database Accession No. BRN: 3888321 Shimizu et al., 64(10):47, 1944.
Pentland, "Photometric Motion" *IEEE Transactions on Pattern Analysis and Machine Intelligence* 13(9):879-890, Sep. 1991.

* cited by examiner

*Primary Examiner*—James O Wilson
*Assistant Examiner*—Tamthom N Truong
(74) *Attorney, Agent, or Firm*—Vinit Kathardekar; Dennis Shelton

(57) ABSTRACT

New substituted quinazoline, quinoxaline, quinoline and isoquinoline compounds, compositions and methods of inhibition of Raf kinase activity in a human or animal subject are provided. The new compounds compositions may be used either alone or in combination with at least one additional agent for the treatment of a Raf kinase mediated disorder, such as cancer.

17 Claims, No Drawings

2,6-DISUBSTITUTED QUINAZOLINES, QUINOXALINES, QUINOLINES AND ISOQUINOLINES AND METHODS OF THEIR USE AS INHIBITORS OF RAF KINASE

CROSS-REFERENCE TO RELATED APPLICATION

This application claims the benefit of U.S. Provisional Application No. 60/511,851, filed Oct. 16, 2003.

FIELD OF THE INVENTION

The present invention relates to new substituted quinazoline, quinoxaline, quinoline and isoquinoline compounds and pharmaceutically acceptable salts, esters or prodrugs thereof, compositions of the new compounds together with pharmaceutically acceptable carriers, and uses of the new compounds, either alone or in combination with at least one additional therapeutic agent, in the prophylaxis or treatment of cancer.

BACKGROUND OF THE INVENTION

The Raf serine/threonine kinases are essential components of the Ras/Mitogen-Activated Protein Kinase (MAPK) signaling module that controls a complex transcriptional program in response to external cellular stimuli. Raf genes code for highly conserved serine-threonine-specific protein kinases which are known to bind to the ras oncogene. They are part of a signal transduction pathway believed to consist of receptor tyrosine kinases, p21 ras, Raf protein kinases, Mek1 (ERK activator or MAPKK) kinases and ERK (MAPK) kinases, which ultimately phosphorylate transcription factors. In this pathway Raf kinases are activated by Ras and phosphorylate and activate two isoforms of Mitogen-Activated Protein Kinase Kinase (called Mek1 and Mek2), that are dual specificity threonine/tyrosine kinases. Both Mek isoforms activate Mitogen Activated Kinases 1 and 2 (MAPK, also called Extracellular Ligand Regulated Kinase 1 and 2 or Erk1 and Erk2). The MAPKs phosphorylate many substrates including transcription factors and in so doing set up their transcriptional program. Raf kinase participation in the Ras/MAPK pathway influences and regulates many cellular functions such as proliferation, differentiation, survival, oncogenic transformation and apoptosis.

Both the essential role and the position of Raf in many signaling pathways have been demonstrated from studies using deregulated and dominant inhibitory Raf mutants in mammalian cells as well as from studies employing biochemical and genetic techniques model organisms. In many cases, the activation of Raf by receptors that stimulate cellular tyrosine phosphorylation is dependent on the activity of Ras, indicating that Ras functions upstream of Raf. Upon activation, Raf-1 then phosphorylates and activates Mek1, resulting in the propagation of the signal to downstream effectors, such as MAPK (mitogen-activated protein kinase) (Crews et al. (1993) Cell 74:215). The Raf serine/threonine kinases are considered to be the primary Ras effectors involved in the proliferation of animal cells (Avruch et al. (1994) Trends Biochem. Sci. 19:279).

Raf kinase has three distinct isoforms, Raf-1 (c-Raf), A-Raf, and B-Raf, distinguished by their ability to interact with Ras, to activate MAPK kinase pathway, tissue distribution and sub-cellular localization (Marias et al., Biochem. J. 351: 289-305, 2000; Weber et. al., Oncogene 19:169-176, 2000; Pritchard et al., Mol. Cell. Biol. 15:6430-6442, 1995).

Recent studies have shown that B-Raf mutation in the skin nevi is a critical step in the initiation of melanocytic neoplasia (Pollock et. al., Nature Genetics 25: 1-2, 2002). Furthermore, most recent studies have emerged that activating mutation in the kinase domain of B-Raf occurs in ~66% of melanomas, 12% of colon carcinoma and 14% of liver cancer (Davies et. al., Nature 417:949-954, 2002) (Yuen et. al., Cancer Research 62:6451-6455, 2002) (Brose et. al., Cancer Research 62:6997-7000, 2002).

Inhibitors of Raf/MEK/ERK pathway at the level of Raf kinases can potentially be effective as therapeutic agents against tumors with over-expressed or mutated receptor tyrosine kinases, activated intracellular tyrosine kinases, tumors with aberrantly expressed Grb2 (an adapter protein that allows stimulation of Ras by the Sos exchange factor) as well as tumors harboring activating mutations of Raf itself. In early clinical trails an inhibitor of Raf-1 kinase, that also inhibits B-Raf, has shown promise as a therapeutic agent in cancer therapy (Crump, Current Pharmaceutical Design 8: 2243-2248, 2002; Sebastien et. al., Current Pharmaceutical Design 8: 2249-2253, 2002).

Disruption of Raf expression in cell lines through the application of RNA antisense technology has been shown to suppress both Ras and Raf-mediated tumorigenicity (Kolch et al., Nature 349:416-428, 1991; Monia et al., Nature Medicine 2(6):668-675, 1996).

Several Raf kinase inhibitors have been described as exhibiting efficacy in inhibiting tumor cell proliferation in vitro and/or in vivo assays (see, e.g., U.S. Pat. Nos. 6,391,636, 6,358,932, 6,037,136, 5,717,100, 6,458,813, 6,204,467, and 6,268,391). Other patents and patent applications suggest the use of Raf kinase inhibitors for treating leukemia (see, e.g., U.S. Pat. Nos. 6,268,391, and 6,204,467, and published U.S. Patent Application Nos. 20020137774; 20020082192; 20010016194; and 20010006975), or for treating breast cancer (see, e.g., U.S. Pat. Nos. 6,358,932, 5,717,100, 6,458,813, 6,268,391, and 6,204,467, and published U.S. Patent Application No. 20010014679).

SUMMARY OF THE INVENTION

New substituted quinazoline, quinoxaline, quinoline and isoquinoline compounds of are provided of the formula (I):

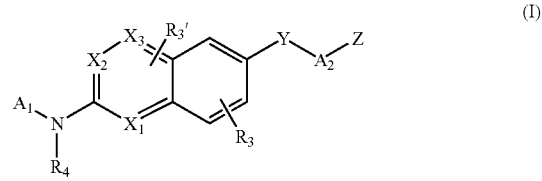

(I)

wherein, $X_1$ and $X_2$ are independently selected from N or CH, provided that at least one of $X_1$ and $X_2$ is N;

Y is O, S, $CH_2$, $NR_5$, —$N(R_5)C(=O)$— or —$C(=O)N(R_5)$—;

Z is

NR₆R₇, NR₅(C=O)R₈, NR₅(C=S)R₈, or NR₅-AA, wherein AA is a substituted or unsubstituted amino acid;

A₁ is substituted or unsubstituted alkyl, cycloalkyl, heterocycloalkyl, aryl, polycyclic aryl, polycyclic arylalkyl, heteroaryl, biaryl, heteroarylaryl, heteroarylheteroaryl, cycloalkylalkyl, cycloalkylaryl, heterocycloalkyl, heterocycloalkylalkyl, heterocycloaryl, arylalkyl, heteroarylalkyl, biarylalkyl, or heteroarylarylalkyl;

A₂ is substituted or unsubstituted aryl or heteroaryl;

R₁ is O or H, and R₂ is NR₆R₇ or hydroxyl; or R₁ is taken together with R₂ to form a substituted or unsubstituted heterocycloalkyl or heteroaryl group; wherein, the dashed line represents a single or double bond;

R₃ and R₃' are independently selected from hydrogen, halogen, loweralkyl, or loweralkoxy;

R₄ is hydrogen, hydroxyl or substituted or unsubstituted alkyl;

R₅ is hydrogen, —C(=O)(R₅ₐ)—, or substituted or unsubstituted alkyl, alkoxyalkyl, aminoalkyl, cycloalkyl, heterocycloalkyl, aryl, heteroaryl, alkyloxyalkylheterocyclo, and heteroarylalkyl, where R₅ₐ is substituted or unsubstituted alkyl, alkoxyalkyl, aminoalkyl, cycloalkyl, heterocycloalkyl, aryl, heteroaryl, alkyloxyalkylheterocyclo, and heteroarylalkyl;

R₆ and R₇ are independently selected from hydrogen, and substituted or unsubstituted alkyl, alkoxy, alkoxyalkyl, aminoalkyl, amidoalkyl, acyl, cycloalkyl, heterocycloalkyl, aryl, heteroaryl, alkyloxyalkylheterocyclo, and heteroarylalkyl; or R₆ and R₇ are taken together to form substituted or unsubstituted heterocyclo or heteroaryl; and R₈ is substituted or unsubstituted alkyl, alkenyl, alkynyl, alkoxy, amino, alkoxyalkyl, aminoalkyl, alkylaminoalkyl, dialkylaminoalkyl, cycloalkyl, cycloalkyloxy, cycloalkylamino, dicycloalkylamino, cycloalkyloxyalkyl, cycloalkylaminoalkyl, dicycloalkylaminoalkyl, (alkyl)(cycloalkyl)aminoalkyl, heterocycloalkyl, heterocycloalkyloxy, heterocycloalkylamino, diheterocycloalkylamino, heterocycloalkyloxyalkyl, heterocycloalkylaminoalkyl, (alkyl)(heterocycloalkyl)aminoalkyl, diheterocyloalkylaminoalkyl, aryl, aryloxy, arylamino, diarylamino, aryloxyalkyl, arylaminoalkyl, diarylaminoalkyl, (alkyl)(aryl)aminoalkyl, heteroaryl, heteroaryloxy, heteroarylamino, diheteroarylamino, (alkyl)(heteroaryl)aminoalkyl, heteroaryloxyalkyl, heteroaryl-aminoalkyl, diheteroarylaminoalkyl, (aryl)(heteroaryl)aminoalkyl or a stereoisomer, tautomer, prodrug or pharmaceutically acceptable salt thereof.

In other embodiments, new substituted quinazoline or isoquinoline compounds are provided of the formula (II):

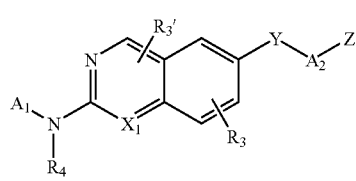

(II)

wherein X₁, Y, Z, A₁, A₂, R₃, R₃' and R₄ are as defined above; or a stereoisomer, tautomer, prodrug or pharmaceutically acceptable salt thereof.

In other embodiments, new substituted quinazoline and quinoline compounds are provided of the formula (III):

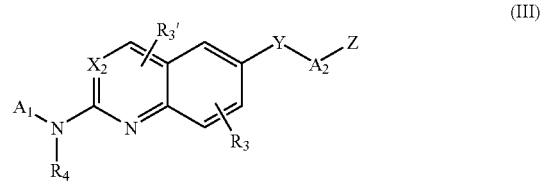

(III)

wherein X₂, Y, Z, A₁, A₂, R₃, R₃' and R₄ are as defined above; or a stereoisomer, tautomer, prodrug or pharmaceutically acceptable salt thereof.

In other embodiments, new substituted quinazoline and quinoxaline compounds are provided of the formulas (IV) and (IVa):

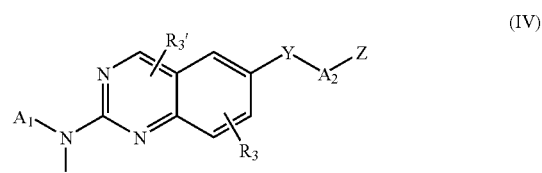

(IV)

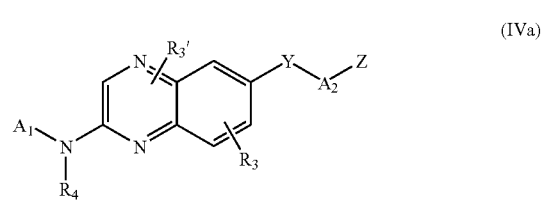

(IVa)

wherein and Y, Z, A₁, A₂, R₃, R₃', and R₄ are as defined above; or a stereoisomer, tautomer, prodrug or pharmaceutically acceptable salt thereof.

In yet other embodiments, new substituted quinazoline, quinoxaline, quinoline and isoquinoline compounds are provided of the formula (V):

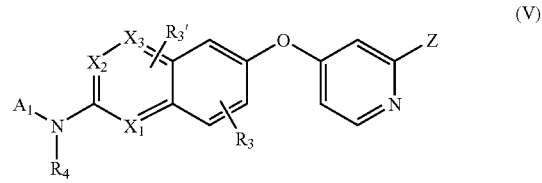

(V)

wherein X₁, X₂, X₃, Z, A₁, R₃, R₃', and R₄ are as defined above; or a pharmaceutically acceptable salt, ester, or prodrugs thereof.

In yet other embodiments, new substituted quinazoline and isoquinoline compounds are provided of the formula (VI):

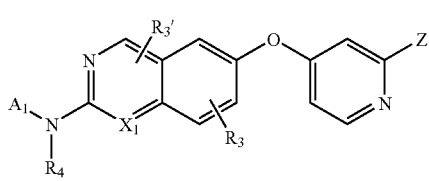

(VI)

wherein $X_1$, $Z$, $A_1$, $R_3$, $R_{3'}$, and $R_4$ are as defined above; or a stereoisomer, tautomer, prodrug or pharmaceutically acceptable salt thereof.

In yet other embodiments, new substituted quinazoline and quinoline compounds are provided of the formula (VII):

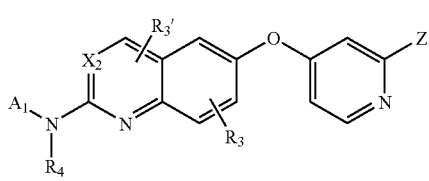

(VII)

wherein $X_2$, $Z$, $A_1$, $R_3$, $R_{3'}$ and $R_4$ are as defined above; or a stereoisomer, tautomer, prodrug or pharmaceutically acceptable salt thereof.

In yet other embodiments, new substituted quinazoline and quinoxaline compounds are provided of the formulas (VIII) and (VIIIa):

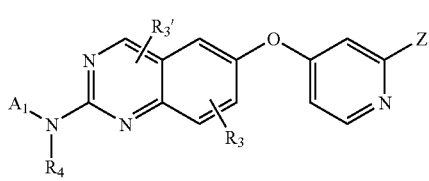

(VIII)

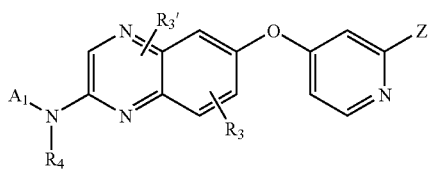

(VIIIa)

wherein $Z$, $A_1$, $R_3$, $R_{3'}$ and $R_4$ are as defined above; or a stereoisomer, tautomer, prodrug or pharmaceutically acceptable salt thereof.

In other aspects, the present invention provides methods for treating Raf related disorders in a human or animal subject in need of such treatment comprising administering to said subject an amount of a compound of formulas (I)-(VIII) effective to reduce or prevent tumor growth in the subject.

In yet other aspects, the present invention provides methods for treating Raf related disorders in a human or animal subject in need of such treatment comprising administering to said subject an amount of a compound of formulas (I)-(VIII) effective to reduce or prevent tumor growth in the subject in combination with at least one additional agent for the treatment of cancer.

In yet other aspects, the present invention provides therapeutic compositions comprising at least one compound of formulas (I)-(VIII) in combination with one or more additional agents for the treatment of cancer, as are commonly employed in cancer therapy.

The compounds of the invention are useful in the treatment of cancers, including carcinomas (e.g., of the lungs, pancreas, thyroid, bladder or colon), myeloid disorders (e.g., myeloid leukemia) and adenomas (e.g., villous colon adenoma).

The invention further provides compositions, methods of use, and methods of manufacture as described in the detailed description of the invention.

DETAILED DESCRIPTION OF THE PREFERRED EMBODIMENT

In accordance with one aspect of the present invention, new substituted quinazoline, quinoxaline, quinoline and isoquinoline compounds and pharmaceutically acceptable salts, esters or prodrugs thereof are provided of the formula (I):

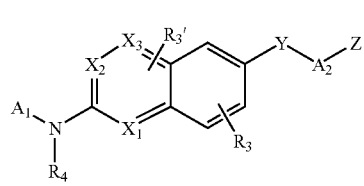

(I)

wherein, $X_1$ and $X_2$ are independently selected from N or CH, provided that at least one of $X_1$ and $X_2$ is N;

Y is O, S, $CH_2$, $NR_5$, $—N(R_5)C(=O)—$ or $—C(=O)N(R_5)—$;

Z is

$NR_6R_7$, $NR_5(C=O)R_8$, $NR_5(C=S)R_8$, or $NR_5$-AA, wherein AA is a substituted or unsubstituted amino acid;

$A_1$ is substituted or unsubstituted alkyl, cycloalkyl, heterocycloalkyl, aryl, polycyclic aryl, polycyclic arylalkyl, heteroaryl, biaryl, heteroarylaryl, heteroarylheteroaryl, cycloalkylalkyl, cycloalkylaryl, heterocycloalkyl, heterocycloalkylalkyl, heterocycloaryl, arylalkyl, heteroarylalkyl, biarylalkyl, or heteroarylarylalkyl;

$A_2$ is substituted or unsubstituted aryl or heteroaryl;

$R_1$ is O or H, and $R_2$ is $NR_6R_7$ or hydroxyl; or $R_1$ is taken together with $R_2$ to form a substituted or unsubstituted heterocycloalkyl or heteroaryl group; wherein, the dashed line represents a single or double bond;

$R_3$ and $R_{3'}$ are independently selected from hydrogen, halogen, loweralkyl, or loweralkoxy;

$R_4$ is hydrogen, hydroxyl or substituted or unsubstituted alkyl;

$R_5$ is hydrogen, $—C(=O)(R_{5a})—$, or substituted or unsubstituted alkyl, alkoxyalkyl, aminoalkyl, cycloalkyl, heterocycloalkyl, aryl, heteroaryl, alkyloxyalkylheterocyclo, and heteroarylalkyl, where $R_{5a}$ is substituted or unsubstituted alkyl, alkoxyalkyl, aminoalkyl, cycloalkyl, heterocycloalkyl, aryl, heteroaryl, alkyloxyalkylheterocyclo, and heteroarylalkyl;

$R_6$ and $R_7$ are independently selected from hydrogen, and substituted or unsubstituted alkyl, alkoxy, alkoxyalkyl, aminoalkyl, amidoalkyl, acyl, cycloalkyl, heterocycloalkyl, aryl, heteroaryl, alkyloxyalkylheterocyclo, and heteroarylalkyl; or $R_6$ and $R_7$ are taken together to form substituted or unsubstituted heterocyclo or heteroaryl; and $R_8$ is substituted or unsubstituted alkyl, alkenyl, alkynyl, alkoxy, amino, alkoxyalkyl, aminoalkyl, alkylaminoalkyl, dialkylaminoalkyl, cycloalkyl, cycloalkyloxy, cycloalkylamino, dicycloalkylamino, cycloalkyloxyalkyl, cycloalkylaminoalkyl, dicycloalkylaminoalkyl, (alkyl)(cycloalkyl)aminoalkyl, heterocycloalkyl, heterocycloalkyloxy, heterocycloalkylamino, diheterocycloalkylamino, heterocycloalkyloxyalkyl, heterocycloalkylaminoalkyl, (alkyl)(heterocycloalkyl)aminoalkyl, diheterocyloalkylaminoalkyl, aryl, aryloxy, arylamino, diarylamino, aryloxyalkyl, arylaminoalkyl, diarylaminoalkyl, (alkyl)(aryl)aminoalkyl, heteroaryl, heteroaryloxy, heteroarylamino, diheteroarylamino, (alkyl)(heteroaryl)aminoalkyl, heteroaryloxyalkyl, heteroaryl-aminoalkyl, diheteroarylaminoalkyl, (aryl)(heteroaryl)aminoalkyl or a stereoisomer, tautomer, prodrug or pharmaceutically acceptable salt thereof.

In other embodiments, new substituted quinazoline and isoquinoline compounds are provided of the formula (II):

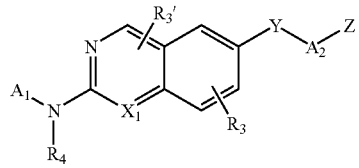

(II)

wherein $X_1$, Y, Z, $A_1$, $A_2$, $R_3$, $R_{3'}$ and $R_4$ are as defined above; or a stereoisomer, tautomer, prodrug or pharmaceutically acceptable salt thereof.

In other embodiments, new substituted quinazoline and quinoline compounds are provided of the formula (III):

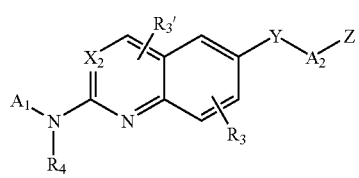

(III)

wherein $X_2$, Y, Z, $A_1$, $A_2$, $R_3$, $R_{3'}$ and $R_4$ are as defined above; or a stereoisomer, tautomer, prodrug or pharmaceutically acceptable salt thereof.

In other embodiments, new substituted quinazoline and quinoxaline compounds are provided of the formulas (IV) and (IVa):

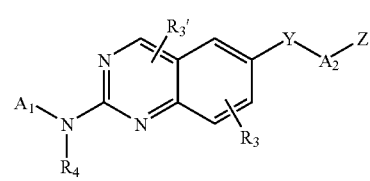

(IV)

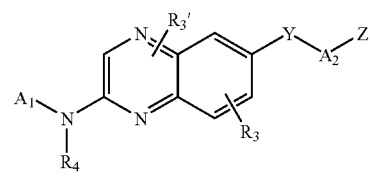

(IVa)

wherein and Y, Z, $A_1$, $A_2$, $R_3$, $R_{3'}$ and $R_4$ are as defined above; or a stereoisomer, tautomer, prodrug or pharmaceutically acceptable salt thereof.

In yet other embodiments, new substituted quinazoline, quinoxaline, quinoline and isoquinoline compounds are provided of the formula (V):

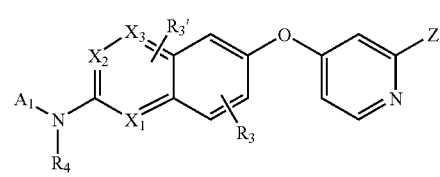

(V)

wherein $X_1$, $X_2$, $X_3$, Z, $A_1$, $R_3$, $R_{3'}$ and $R_4$ are as defined above; or a pharmaceutically acceptable salt, ester, or prodrugs thereof.

In yet other embodiments, new substituted quinazoline compounds are provided of the formula (VI):

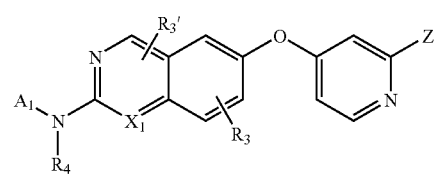

(VI)

wherein $X_1$, Z, $A_1$, $R_3$, $R_{3'}$ and $R_4$ are as defined above; or
a stereoisomer, tautomer, prodrug or pharmaceutically acceptable salt thereof.

In yet other embodiments, new substituted quinazoline and quinoline compounds are provided of the formula (VII):

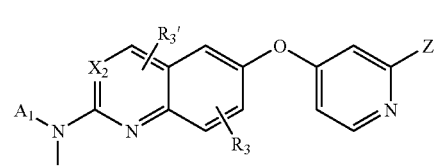

(VII)

wherein $X_2$, $A_1$, $R_1$, $R_2$, $R_3$, $R_{3'}$ and $R_4$ are as defined above; or a stereoisomer, tautomer, prodrug or pharmaceutically acceptable salt thereof.

In yet other embodiments, new substituted quinazoline and quinoxaline compounds are provided of the formulas (VIII) and (VIIIa):

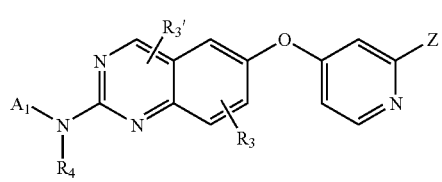
(VIII)

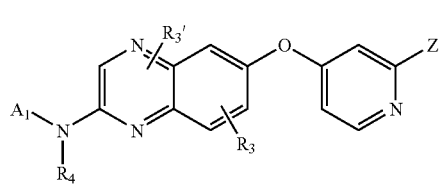
(VIIIa)

wherein Z, $A_1$, $R_3$, $R_{3'}$ and $R_4$ are as defined above; or a stereoisomer, tautomer, prodrug or pharmaceutically acceptable salt thereof.

In another aspect, the present invention provides methods of treating human or animal subjects suffering from a Raf related disorder, such as cancer. Thus, the present invention provides methods of treating a human or animal subject in need of such treatment comprising administering to the subject a therapeutically effective amount of a compound of formulas (I)-(VIII) above, either alone or in combination with other anticancer agents.

In other aspects, the present invention provides methods for treating Raf related disorders in a human or animal subject in need of such treatment comprising administering to said subject an amount of a compound of formulas (I)-(VIII) effective to reduce or prevent tumor growth in the subject.

In yet other aspects, the present invention provides methods for treating Raf related disorders in a human or animal subject in need of such treatment comprising administering to said subject an amount of a compound of formulas (I)-(VIII) effective to reduce or prevent tumor growth in the subject in combination with at least one additional agent for the treatment of cancer. A number of suitable anticancer agents to be used as combination therapeutics are contemplated for use in the methods of the present invention. Indeed, the present invention contemplates, but is not limited to, administration of numerous anticancer agents such as: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons [e.g. IFN-a, etc.] and interleukins [e.g. IL-2, etc.], etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other examples of chemotherapeutic compounds and anticancer therapies suitable for coadministration with the disclosed compounds of formulas (I)-(VIII) are known to those skilled in the art.

In preferred embodiments, anticancer agents to be used in combination with compounds of the present invention comprise agents that induce or stimulate apoptosis. Agents that induce apoptosis include, but are not limited to, radiation; kinase inhibitors (e.g., epidermal growth factor receptor [EGFR] kinase inhibitor, vascular endothelial growth factor receptor [VEGFR] kinase inhibitor, fibroblast growth factor receptor [FGFR] kinase inhibitor, platelet-derived growth factor receptor [PGFR] I kinase inhibitor, and Bcr-Abl kinase inhibitors such as Gleevec® [imatinib mesylate or STI-571]); antisense molecules; antibodies [e.g., Herceptine anti-HER monoclonal antibody and Rituxan® anti-CD20 monoclonal antibody]; anti-estrogens [e.g., raloxifene and tamoxifen]; anti-androgens [e.g., flutamide, bicalutamide, finasteride, amino-glutethamide, ketoconazole, and corticosteroids]; cyclooxygenase 2 (COX-2) inhibitors [e.g., Celecoxib®, meloxicam, NS-398, and non-steroidal antiinflammatory drugs (NSAIDs)]; and cancer chemotherapeutic drugs [e.g., irinotecan (Camptosar®), CPT-11, fludarabine (Fludara®), dacarbazine (DTIC®), dexamethasone, mitoxantrone, Mylotarg®, VP-16, cisplatinum, 5-FU, doxorubicin, docetaxel (Taxotere®) or taxol, dacarbazine, aldesleukin, capecitabine, and Iressa® (gefitinib)]; cellular signaling molecules; ceramides and cytokines; and staurosprine, and the like.

In other aspects, the present invention provides pharmaceutical compositions comprising at least one compound of formulas (I)-(VIII) together with a pharmaceutically acceptable carrier suitable for administration to a human or animal subject, either alone or together with other anticancer agents.

In other aspects, the present invention provides methods of manufacture of compounds of formulas (I)-(VIII) as described herein.

In yet other aspects, the present invention provides compounds which are inhibitors of the enzyme raf kinase. Since the enzyme is a downstream effector of p21$^{ras}$, the instant inhibitors are useful in pharmaceutical compositions for human or veterinary use where inhibition of the raf kinase pathway is indicated, e.g., in the treatment of tumors and/or cancerous cell growth mediated by raf kinase. In particular, the compounds are useful in the treatment of human or animal, e.g., murine cancer, since the progression of these cancers is dependent upon the ras protein signal transduction cascade and therefore is susceptible to treatment by interruption of the cascade by inhibiting raf kinase activity. Accordingly, the compounds of the invention are useful in treating solid cancers, such as, for example, carcinomas (e.g., of the lungs, pancreas, thyroid, bladder or colon, myeloid disorders (e.g., myeloid leukemia) or adenomas (e.g., villous colon adenoma).

"Raf inhibitor" is used herein to refer to a compound that exhibits an IC$_{50}$ with respect to Raf Kinase activity of no more than about 100 µM and more typically not more than about 50 µM, as measured in the Raf/Mek Filtration Assay described generally hereinbelow. Preferred isoforms of Raf Kinase in which the compounds of the present invention will be shown to inhibit, include A-Raf, B-Raf, and C-Raf (Raf-1). "IC$_{50}$" is that concentration of inhibitor which reduces the activity of an enzyme (e.g., Raf kinase) to half-maximal level. Representative compounds of the present invention have been discovered to exhibit inhibitory activity against Raf. Compounds of the present invention preferably exhibit an IC$_{50}$ with respect to Raf of no more than about 10 µM, more preferably, no more than about 5 µM, even more preferably not more than about 1 µM, and most preferably, not more than about 200 nM, as measured in the Raf kinase assays described herein.

The phrase "alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH$(CH_3)_2$, —CH$(CH_3)(CH_2CH_3)$, —CH$(CH_2CH_3)_2$, —C$(CH_3)_3$, —C$(CH_2CH_3)_3$, —CH$_2$CH$(CH_3)_2$, —CH$_2$CH$(CH_3)(CH_2CH_3)$, —CH$_2$CH$(CH_2CH_3)_2$, —CH$_2$C$(CH_3)_3$, —CH$_2$C$(CH_2CH_3)_3$, —CH$(CH_3)$CH$(CH_3)(CH_2CH_3)$, —CH$_2$CH$_2$CH$(CH_3)_2$, —CH$_2$CH$_2$CH$(CH_3)(CH_2CH_3)$, —CH$_2$CH$_2$CH$(CH_2CH_3)_2$, —CH$_2$CH$_2$C$(CH_3)_3$, —CH$_2$CH$_2$C$(CH_2CH_3)_3$, —CH$(CH_3)$CH$_2$CH$(CH_3)_2$, —CH$(CH_3)$CH$(CH_3)$CH$(CH_3)_2$, —CH$(CH_2CH_3)$CH$(CH_3)$CH$(CH_3)(CH_2CH_3)$, and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. Thus the phrase alkyl groups includes primary alkyl groups, secondary alkyl groups, and tertiary alkyl groups. Preferred alkyl groups include straight and branched chain alkyl groups and cyclic alkyl groups having 1 to 12 carbon atoms.

As used herein "loweralkyl" includes both substituted or unsubstituted straight or branched chain alkyl groups having from 1 to 6 carbon atoms. Representative loweralkyl groups include, for example, methyl, ethyl, propyl, isopropyl, n-butyl, tert-butyl, neopentyl, trifluoromethyl, pentafluoroethyl and the like. Loweralkyl groups may be substituted, such as with halo, hydroxy, amino, nitro and/or cyano groups, and the like. Representative of halo-substituted and hydroxy-substituted loweralkyl include chloromethyl, trichloromethyl, chloroethyl, hydroxyethyl, and the like. Other suitable substituted loweralkyl moieties include, for example, aralkyl, aminoalkyl, aminoaralkyl, carbonylaminoalkyl, alkylcarbonylaminoalkyl, arylcarbonylaminoalkyl, aralkylcarbonylaminoalkyl, aminoalkoxyalkyl and arylaminoalkyl.

"Loweralkoxy" as used herein refers to RO— wherein R is loweralkyl. Representative examples of loweralkoxy groups include methoxy, ethoxy, t-butoxy, trifluoromethoxy and the like.

As used herein, the term "halogen" or "halo" refers to chloro, bromo, fluoro and iodo groups. "Haloalkyl" refers to an alkyl radical substituted with one or more halogen atoms. The term "haloloweralkyl" refers to a loweralkyl radical substituted with one or more halogen atoms. The term "haloalkoxy" refers to an alkoxy radical substituted with one or more halogen atoms. The term "haloloweralkoxy" refers to a loweralkoxy radical substituted with one or more halogen atoms.

"Amino" refers herein to the group —NH$_2$. The term "alkylamino" refers herein to the group —NRR' where R and R' are each independently selected from hydrogen or a lower alkyl. The term "arylamino" refers herein to the group —NRR' where R is aryl and R' is hydrogen, a lower alkyl, or an aryl. The term "aralkylamino" refers herein to the group —NRR' where R is a lower aralkyl and R' is hydrogen, a loweralkyl, an aryl, or a loweraralkyl.

The term amino acid refers to both alpha and beta amino acids having D- or L-stereochemistry, and includes, but is not limited to, synthetic, non-natural amino acids having side chains other than those found in the 20 common amino acids. Non-natural amino acids are commercially available or may be prepared according to U.S. Pat. No. 5,488,131 and references therein. Amino acids may be further substituted to contain modifications to their amino, carboxy, or side chain groups. These modifications include the numerous protecting groups commonly used in peptide synthesis.

The term "alkoxyalkyl" refers to the group -alk$_1$-O-alk$_2$ where alk$_1$ is alkyl or alkenyl, and alk$_2$ is alkyl or alkenyl. The term "loweralkoxyalkyl" refers to an alkoxyalkyl where alk$_1$ is loweralkyl or loweralkenyl, and alk$_2$ is loweralkyl or loweralkenyl. The term "aryloxyalkyl" refers to the group -alkyl-O-aryl. The term "aralkoxyalkyl" refers to the group -alkylenyl-O-aralkyl, where aralkyl is a loweraralkyl.

The term "alkoxyalkylamino" refers herein to the group —NR-(alkoxyalkyl), where R is typically hydrogen, loweraralkyl, or loweralkyl. The term "aminoloweralkoxyalkyl" refers herein to an aminoalkoxyalkyl in which the alkoxyalkyl is a loweralkoxyalkyl.

The term "aminocarbonyl" refers herein to the group —C(O)—NH$_2$. "Substituted aminocarbonyl" refers herein to the group —C(O)—NRR' where R is loweralkyl and R' is hydrogen or a loweralkyl. The term "arylaminocarbonyl" refers herein to the group —C(O)—NRR' where R is an aryl and R' is hydrogen, loweralkyl or aryl. "aralkylaminocarbonyl" refers herein to the group —C(O)—NRR' where R is loweraralkyl and R' is hydrogen, loweralkyl, aryl, or loweraralkyl.

"Aminosulfonyl" refers herein to the group —S(O)$_2$—NH$_2$. "Substituted aminosulfonyl" refers herein to the group —S(O)$_2$—NRR' where R is loweralkyl and R' is hydrogen or a loweralkyl. The term "aralkylaminosulfonlyaryl" refers herein to the group -aryl-S(O)$_2$—NH-aralkyl, where the aralkyl is loweraralkyl.

"Carbonyl" refers to the divalent group —C(O)—.

"Carbonyloxy" refers generally to the group —C(O)—O. Such groups include esters, —C(O)—O—R, where R is loweralkyl, cycloalkyl, aryl, or loweraralkyl. The term "carbonyloxycycloalkyl" refers generally herein to both a "carbonyloxycarbocycloalkyl" and a "carbonyloxyheterocycloalkyl", i.e., where R is a carbocycloalkyl or heterocycloalkyl, respectively. The term "arylcarbonyloxy" refers herein to the group —C(O)—O-aryl, where aryl is a mono- or polycyclic, carbocycloaryl or heterocycloaryl. The term "aralkylcarbonyloxy" refers herein to the group —C(O)—O-aralkyl, where the aralkyl is loweraralkyl.

The term "sulfonyl" refers herein to the group —SO$_2$—. "Alkylsulfonyl" refers to a substituted sulfonyl of the structure —SO$_2$R— in which R is alkyl. Alkylsulfonyl groups employed in compounds of the present invention are typically loweralkylsulfonyl groups having from 1 to 6 carbon atoms in its backbone structure. Thus, typical alkylsulfonyl groups employed in compounds of the present invention include, for example, methylsulfonyl (i.e., where R is methyl), ethylsulfonyl (i.e., where R is ethyl), propylsulfonyl (i.e., where R is propyl), and the like. The term "arylsulfonyl" refers herein to the group —SO$_2$-aryl. The term "aralkylsulfonyl" refers herein to the group —SO$_2$-aralkyl, in which the aralkyl is loweraralkyl. The term "sulfonamido" refers herein to —SO$_2$NH$_2$.

As used herein, the term "carbonylamino" refers to the divalent group —NH—C(O)— in which the hydrogen atom of the amide nitrogen of the carbonylamino group can be replaced a loweralkyl, aryl, or loweraralkyl group. Such groups include moieties such as carbamate esters (—NH—C(O)—O—R) and amides —NH—C(O)—O—R, where R is a straight or branched chain loweralkyl, cycloalkyl, or aryl or loweraralkyl. The term "loweralkylcarbonylamino" refers to alkylcarbonylamino where R is a loweralkyl having from 1 to about 6 carbon atoms in its backbone structure. The term "arylcarbonylamino" refers to group —NH—C(O)—R where R is an aryl. Similarly, the term "aralkylcarbonylamino" refers to carbonylamino where R is a lower aralkyl. As used herein, the term "aminocarbonyl" refers to the divalent group —C(O)—NH— in which the hydrogen atom of the amide nitrogen of the carbonylamino group can be replaced a loweralkyl, aryl, or loweraralkyl group, as described above.

As used herein, the term "guanidino" or "guanidyl" refers to moieties derived from guanidine, $H_2N-C(=NH)-NH_2$. Such moieties include those bonded at the nitrogen atom carrying the formal double bond (the "2"-position of the guanidine, e.g., diaminomethyleneamino, $(H_2N)_2C=NH-$) and those bonded at either of the nitrogen atoms carrying a formal single bond (the "1-" and/or "3"-positions of the guandine, e.g., $H_2N-C(=NH)-NH-$). The hydrogen atoms at any of the nitrogens can be replaced with a suitable substituent, such as loweralkyl, aryl, or loweraralkyl.

As used herein, the term "amidino" refers to the moieties $R-C(=N)-NR'-$ (the radical being at the "$N^1$" nitrogen) and $R(NR')C=N-$ (the radical being at the "$N^2$" nitrogen), where R and R' can be hydrogen, loweralkyl, aryl, or loweraralkyl.

"Cycloalkyl" refers to a mono- or polycyclic, heterocyclic or carbocyclic alkyl substituent. Typical cycloalkyl substituents have from 3 to 8 backbone (i.e., ring) atoms in which each backbone atom is either carbon or a heteroatom. The term "heterocycloalkyl" refers herein to cycloalkyl substituents that have from 1 to 5, and more typically from 1 to 4 heteroatoms in the ring structure. Suitable heteroatoms employed in compounds of the present invention are nitrogen, oxygen, and sulfur. Representative heterocycloalkyl moieties include, for example, morpholino, piperazinyl, piperadinyl and the like. Carbocycloalkyl groups are cycloalkyl groups in which all ring atoms are carbon. When used in connection with cycloalkyl substituents, the term "polycyclic" refers herein to fused and non-fused alkyl cyclic structures. Examples of such polycyclic structures include bicyclic compounds having two bridgehead atoms connected by three or more arms. An example of a bicyclic structure is bicyclo [2.2.1]heptane, in which the bridgehead atoms are connected by three arms respectively having two, two, and one carbon atoms.

The term "substituted heterocycle" or "heterocyclic group" or heterocycle as used herein refers to any 3- or 4-membered ring containing a heteroatom selected from nitrogen, oxygen, and sulfur or a 5- or 6-membered ring containing from one to three heteroatoms selected from the group consisting of nitrogen, oxygen, or sulfur; wherein the 5-membered ring has 0-2 double bonds and the 6-membered ring has 0-3 double bonds; wherein the nitrogen and sulfur atom maybe optionally oxidized; wherein the nitrogen and sulfur heteroatoms maybe optionally quarternized; and including any bicyclic group in which any of the above heterocyclic rings is fused to a benzene ring or another 5- or 6-membered heterocyclic ring independently defined above. The term "heterocycle" thus includes rings in which nitrogen is the heteroatom as well as partially and fully-saturated rings. Preferred heterocycles include, for example: diazapinyl, pyrryl, pyrrolinyl, pyrrolidinyl, pyrazolyl, pyrazolinyl, pyrazolidinyl, imidazoyl, imidazolinyl, imidazolidinyl, pyridyl, piperidinyl, pyrazinyl, piperazinyl, N-methyl piperazinyl, azetidinyl, N-methylazetidinyl, pyrimidinyl, pyridazinyl, oxazolyl, oxazolidinyl, isoxazolyl, isoazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl and benzothienyl.

Heterocyclic moieties can be unsubstituted or monosubstituted or disubstituted with various substituents independently selected from hydroxy, halo, oxo (C=O), alkylimino (RN=, wherein R is a loweralkyl or loweralkoxy group), amino, alkylamino, dialkylamino, acylaminoalkyl, alkoxy, thioalkoxy, polyalkoxy, loweralkyl, cycloalkyl or haloalkyl.

The heterocyclic groups may be attached at various positions as will be apparent to those having skill in the organic and medicinal chemistry arts in conjunction with the disclosure herein.

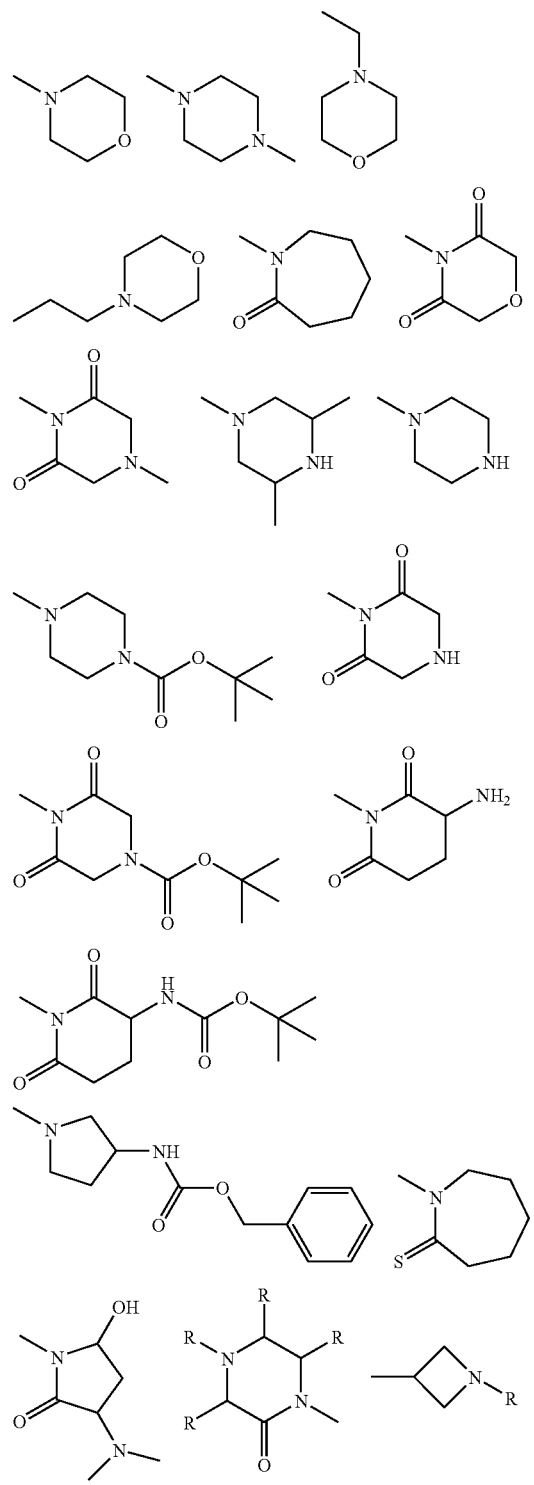

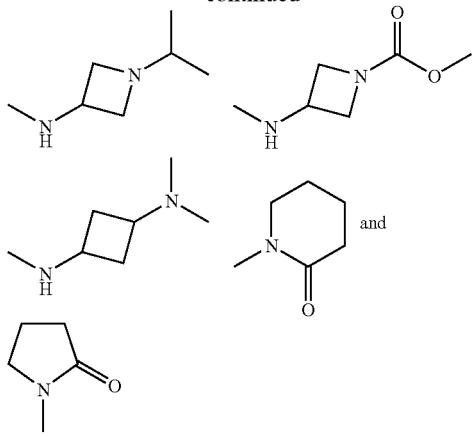

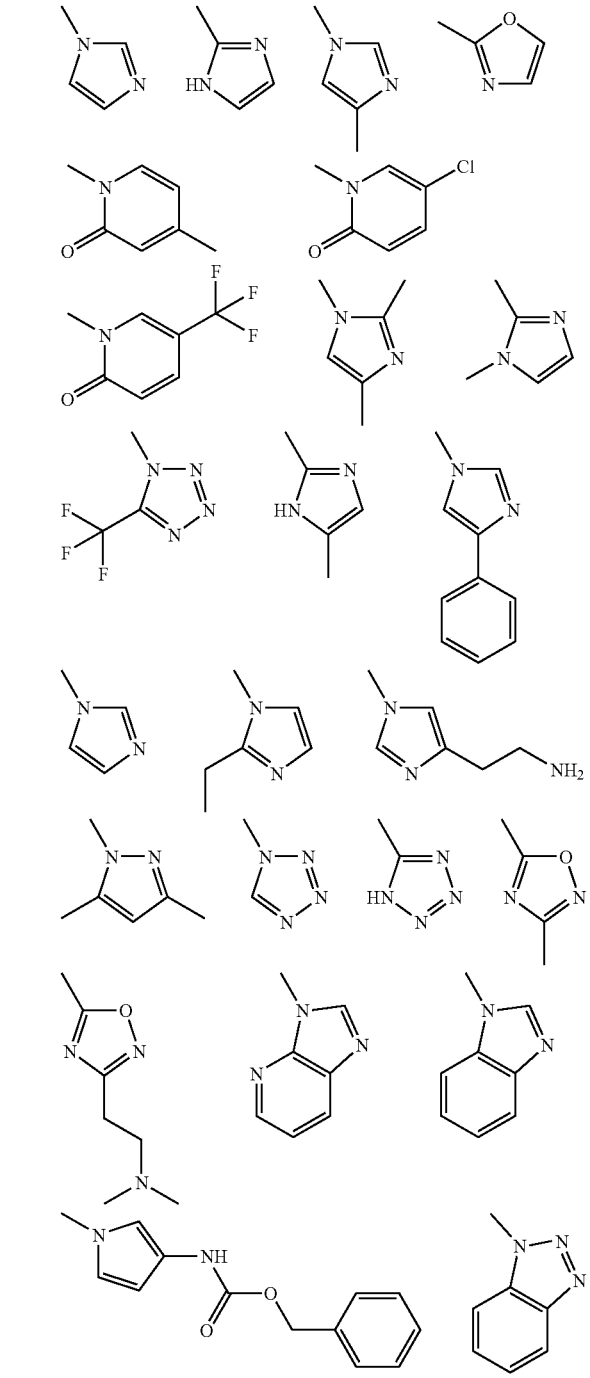

and F where R is H or a heterocyclic substituent, as described herein.

Representative heterocyclics include, for example, imidazolyl, pyridyl, piperazinyl, azetidinyl, thiazolyl, furanyl, triazolyl benzimidazolyl, benzothiazolyl, benzoxazolyl, quinolinyl, isoquinolinyl, quinazolinyl, quinoxalinyl, phthalazinyl, indolyl, naphthpyridinyl, indazolyl, and quinolizinyl.

"Aryl" refers to optionally substituted monocyclic and polycyclic aromatic groups having from 3 to 14 backbone carbon or hetero atoms, and includes both carbocyclic aryl groups and heterocyclic aryl groups. Carbocyclic aryl groups are aryl groups in which all ring atoms in the aromatic ring are carbon. The term "heteroaryl" refers herein to aryl groups having from 1 to 4 heteroatoms as ring atoms in an aromatic ring with the remainder of the ring atoms being carbon atoms. When used in connection with aryl substituents, the term "polycyclic aryl" refers herein to fused and non-fused cyclic structures in which at least one cyclic structure is aromatic, such as, for example, benzodioxozolo (which has a heterocyclic structure fused to a phenyl group, i.e.,

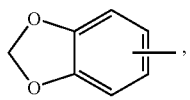

naphthyl, and the like. Exemplary aryl moieties employed as substituents in compounds of the present invention include phenyl, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, and the like.

"Aralkyl" refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

Representative heteroaryl groups include, for example, those shown below. These heteroaryl groups can be further substituted and may be attached at various positions as will be apparent to those having skill in the organic and medicinal chemistry arts in conjunction with the disclosure herein.

Representative heteroaryl groups include, for example, imidazolyl, pyridyl, piperazinyl, azetidinyl, thiazolyl, triazolyl benzimidazolyl, benzothiazolyl, benzoxazolyl, pyrazolyl and pyrazinyl.

The term "biaryl" refers to a group or substituent to which two aryl groups, which are not condensed to each other, are bound. Exemplary biaryl compounds include, for example, phenylbenzene, diphenyldiazene, 4-methylthio-1-phenylbenzene, phenoxy-benzene, (2-phenylethynyl)benzene, diphenyl ketone, (4-phenylbuta-1,3-diynyl)benzene, phenylbenzylamine, (phenylmethoxy)benzene, and the like. Preferred optionally substituted biaryl groups include: 2-(phenylamino)-N-[4-(2-phenylethynyl)phenyl]-acetamide, 1,4-diphenylbenzene, N-[4-(2-phenylethynyl)phenyl]-2-[benzylamino]-acetamide, 2-amino-N-[4-(2-phenylethynyl)phenyl]propanamide, 2-amino-N-[4-(2-phenylethynyl)phenyl]acetamide, 2-(cyclopropylamino)-N-[4-(2-phenylethynyl)phenyl]-acetamide, 2-(ethylamino)-N-[4-(2-phenylethynyl)phenyl]acetamide, 2-[(2-methyl-propyl)amino]-N-[4-(2-phenylethynyl)phenyl]acetamide, 5-phenyl-2H-benzo[d]1,3-dioxolene, 2-chloro-1-methoxy-4-phenylbenzene, 2-[(imidazolylmethyl)amino]-N-[4-(2-phenylethynyl)phenyl]acetamide, 4-phenyl-1-phenoxybenzene, N-(2-aminoethyl)[4-(2-phenylethynyl)phenyl]carboxamide, 2-{[(4-fluorophenyl)methyl]amino}-N-[4-(2-phenylethynyl)phenyl]acetamide, 2-{[(4-methylphenyl)methyl]amino}-N-[4-(2-phenylethynyl)-phenyl]acetamide, 4-phenyl-1-(trifluoromethyl)benzene, 1-butyl-4-phenylbenzene, 2-(cyclohexylamino)-N-[4-(2-phenylethynyl)phenyl]acetamide, 2-(ethylmethylamino)-N-[4-(2-phenylethynyl)phenyl]acetamide, 2-(butylamino)-N-[4-(2-phenylethynyl)phenyl]-acetamide, N-[4-(2-phenylethynyl)phenyl]-2-(4-pyridylamino)acetamide, N-[4-(2-phenylethynyl)phenyl]-2-(quinuclidin-3-ylamino)acetamide, N-[4-(2-phenylethynyl)-phenyl]pyrrolidin-2-ylcarboxamide, 2-amino-3-methyl-N-[4-(2-phenylethynyl)phenyl]-butanamide, 4-(4-phenylbuta-1,3-diynyl)phenylamine, 2-(dimethylamino)-N-[4-(4-phenylbuta-1,3-diynyl)phenyl]acetamide, 2-(ethylamino)-N-[4-(4-phenylbuta-1,3-diynyl)phenyl]acetamide, 4-ethyl-1-phenylbenzene, 1-[4-(2-phenylethynyl)phenyl]ethan-1-one, N-(1-carbamoyl-2-hydroxypropyl) [4-(4-phenylbuta-1,3-diynyl)phenyl]carboxamide, N-[4-(2-phenylethynyl)phenyl]propanamide, 4-methoxyphenyl phenyl ketone, phenyl-N-benzamide, (tert-butoxy)-N-[(4-phenylphenyl)methyl]carboxamide, 2-(3-phenylphenoxy)ethanehydroxamic acid, 3-phenylphenyl propanoate, 1-(4-ethoxyphenyl)-4-methoxybenzene, and [4-(2-phenylethynyl)phenyl]pyrrole.

The term "heteroarylaryl" refers to a biaryl group where one of the aryl groups is a heteroaryl group. Exemplary heteroarylaryl groups include, for example, 2-phenylpyridine, phenylpyrrole, 3-(2-phenylethynyl)pyridine, phenylpyrazole, 5-(2-phenylethynyl)-1,3-dihydropyrimidine-2,4-dione, 4-phenyl-1,2,3-thiadiazole, 2-(2-phenylethynyl)pyrazine, 2-phenylthiophene, phenylimidazole, 3-(2-piperazinylphenyl)furan, 3-(2,4-dichlorophenyl)-4-methylpyrrole, and the like. Preferred optionally substituted heteroarylaryl groups include: 5-(2-phenylethynyl)pyrimidine-2-ylaamine, 1-methoxy-4-(2-thienyl)benzene, 1-methoxy-3-(2-thienyl)benzene, 5-methyl-2-phenylpyridine, 5-methyl-3-phenyl-isoxazole, 2-[3-(trifluoromethyl)phenyl]furan, 3-fluoro-5-(2-furyl)-2-methoxy-1-prop-2-enylbenzene, (hydroxyimino)(5-phenyl(2-thienyl))methane, 5-[(4-methylpiperazinyl)methyl]-2-phenylthiophene, 2-(4-ethylphenyl)thiophene, 4-methylthio-1-(2-thienyl)benzene, 2-(3-nitrophenyl)thiophene, (tert-butoxy)-N-[(5-phenyl(3-pyridyl))-methyl]carboxamide, hydroxy-N-[(5-phenyl(3-pyridyl))methyl]amide, 2-(phenylmethylthio)pyridine, and benzylimidazole.

The term "heteroarylheteroaryl" refers to a biaryl group where both of the aryl groups are a heteroaryl group. Exemplary heteroarylheteroaryl groups include, for example, 3-pyridylimidazole, 2-imidazolylpyrazine, and the like. Preferred optionally substituted heteroarylheteroaryl groups include: 2-(4-piperazinyl-3-pyridyl)furan, diethyl-(3-pyrazin-2-yl(4-pyridyl))amine, and dimethyl{2-[2-(5-methylpyrazin-2-yl)ethynyl](4-pyridyl)}amine.

"Optionally substituted" or "substituted" refers to the replacement of hydrogen with a monovalent or divalent radical. Suitable substitution groups include, for example, hydroxyl, nitro, amino, imino, cyano, halo, thio, sulfonyl, thioamido, amidino, imidino, oxo, oxamidino, methoxamidino, imidino, guanidino, sulfonamido, carboxyl, formyl, loweralkyl, haloloweralkyl, loweralkyamino, haloloweralkylamino, loweralkoxy, haloloweralkoxy, loweralkoxyalkyl, alkylcarbonyl, aminocarbonyl, arylcarbonyl, aralkylcarbonyl, heteroarylcarbonyl, heteroaralkylcarbonyl, alkylthio, aminoalkyl, cyanoalkyl, aryl and the like. The term substituted and unsubstituted, when introducing a list of substituents, is intended to apply to each member of that list. For instance the phrase "substituted and unsubstituted aryl, heteroaryl, or alkyl" and the phrase "substituted and unsubstituted aryl, heteroaryl, and alkyl" is intended to specify aryl, heteroaryl, and alky groups that are each substituted or unsubstituted.

The substitution group can itself be substituted. The group substituted onto the substitution group can be carboxyl, halo; nitro, amino, cyano, hydroxyl, loweralkyl, loweralkoxy, aminocarbonyl, —SR, thioamido, —SO$_3$H, —SO$_2$R or cycloalkyl, where R is typically hydrogen, hydroxyl or loweralkyl.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substitutents can be straight chain, branched or cyclic arrangements of covalently bonded carbon or heteroatoms.

As used herein, the term "carboxy-protecting group" refers to a carbonyl group which has been esterified with one of the commonly used carboxylic acid protecting ester groups employed to block or protect the carboxylic acid function while reactions involving other functional sites of the compound are carried out. In addition, a carboxy protecting group can be attached to a solid support whereby the compound remains connected to the solid support as the carboxylate until cleaved by hydrolytic methods to release the corresponding free acid. Representative carboxy-protecting groups include, for example, loweralkyl esters, secondary amides and the like.

As used herein, the term "pharmaceutically acceptable salts" refers to the nontoxic acid or alkaline earth metal salts of the compounds of Formula I. These salts can be prepared in situ during the final isolation and purification of the compounds of Formula I, or by separately reacting the base or acid functions with a suitable organic or inorganic acid or base, respectively. Representative salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "cancer" refers to cancer diseases that can be beneficially treated by the inhibition of Raf kinase, including, for example, solid cancers, such as carcinomas (e.g., of the lungs, pancreas, thyroid, bladder or colon), myeloid disorders (e.g., myeloid leukemia) and adenomas (e.g., villous colon adenoma).

In illustrative embodiments of the invention, $A_1$ may be, for example, phenyl, phenylalkyl, pyridyl, pyrimidinyl, pyridylalkyl, pyrimidinylalkyl, alkylbenzoate, thiophene, thiophene-2-carboxylate, indenyl, 2,3-dihydroindenyl, tetralinyl, triflourophenyl, (triflouromethyl)thiophenyl, morpholinyl, N-piperazinyl, N-morpholinylalkyl, piperazinylalkyl, cyclohexylalkyl, indolyl, 2,3-dihydroindolyl, 1-aceytl-2,3-dihydroindolyl, cycloheptyl, bicyclo[2.2.1]hept-2-yl, pyrrolidinyl, pyrrolidin-1-yl, pyrrolidin-1-ylalkyl, 4-amino(imino)methylphenyl, isoxazolyl, indazolyl, adamantyl, bicyclohexyl, quinuclidinyl, imidazolyl, benzimidazolyl, imidazolylphenyl, phenylimidazolyl, pthalamido, napthyl, napththalenyl, benzophenone, anilinyl, anisolyl, quinolinyl, quinolinonyl, phenylsulfonyl, phenylalkylsulfonyl, 9H-flouren-1-yl, piperidin-1-yl, piperidin-1-ylalkyl, cyclopropyl, cyclopropylalkyl, furanyl, N-methylpiperidin-4-yl, pyrrolidin-4-ylpyridinyl, 4-diazepan-1-yl, hydroxypyrrolidn-1-yl, dialkylaminopyrrolidin-1-yl, and 1,4'-bipiperidin-1'-yl, which may be substituted by one or more substitutents selected from the group consisting of hydroxyl, nitro, cyano, halo, and substituted or unsubstituted amino, imino, thio, sulfonyl, thioamido, amidino, imidino, oxo, oxamidino, methoxamidino, imidino, guanidino, sulfonamido, carboxyl, formyl, loweralkyl, haloloweralkyl, loweralkyamino, haloloweralkylamino, loweralkoxy, haloloweralkoxy, loweralkoxyalkyl, alkylcarbonyl, aminocarbonyl, loweralkylaminocarbonyl, heterocycloalkylloweralkylaminocarbonyl, carboxylloweralkylaminocarbonyl, arylcarbonyl, aralkylcarbonyl, heteroarylcarbonyl, heteroaralkylcarbonyl, alkylthio, aminoalkyl, cyanoalkyl, aryl and the like. In other embodiments, $A_1$ may be substituted phenyl, such as, for example, substituted or unsubstituted hydroxyphenyl, hydroxyalkylphenyl, alkylphenyl, dialkylphenyl, trialkylphenyl, alkoxyphenyl, dialkoxyphenyl, alkoxyalkylphenyl, halophenyl, dihalophenyl, haloalkylphenyl, haloalkoxyphenyl, alkylhalophenyl, alkoxyhalophenyl, alkylthiophenyl, aminophenyl, nitrophenyl, acetylphenyl, sulfamoylphenyl, biphenyl, alkoxybiphenyl, cyclohexylphenyl, phenyloxyphenyl, dialkylaminophenyl, morpholinylphenyl, heterocyclylcarbonylphenyl, heterocyclylphenyl, heterocyclylalkylphenyl, furanylphenyl, (1,4'-bipiperidin-1'-ylcarbonyl)phenyl, pyrimidin-5-ylphenyl, and quinolidinylphenyl. In yet other embodiments, $A_1$ is substituted phenyl selected from the group consisting of chlorophenyl, flourophenyl, bromophenyl, iodophenyl, dichlorophenyl, difluorophenyl, dibromophenyl, flurorchlorophenyl, bromochlorophenyl, trifluoromethylphenyl, trifluoromethoxyphenyl, alkylbromophenyl, trifluoromethylbromophenyl, alkylchlorophenyl, triflouromethylchlorophenyl, alkylflourophenyl, and triflouromethylfluorophenyl.

In other illustrative embodiments of the invention, $A_2$ is substituted or unsubstituted aryl or heteroaryl, such as, for example, substituted or unsubstituted phenyl, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, and the like, which may be substituted by one or more substitutents selected from the group consisting of hydroxyl, nitro, cyano, halo, and substituted or unsubstituted amino, imino, thio, sulfonyl, thioamido, amidino, imidino, oxo, oxamidino, methoxamidino, imidino, guanidino, sulfonamido, carboxyl, formyl, loweralkyl, haloloweralkyl, loweralkyamino, haloloweralkylamino, loweralkoxy, haloloweralkoxy, loweralkoxyalkyl, alkylcarbonyl, aminocarbonyl, loweralkylaminocarbonyl, heterocycloalkylloweralkylaminocarbonyl, carboxylloweralkylaminocarbonyl, arylcarbonyl, aralkylcarbonyl, heteroarylcarbonyl, heteroaralkylcarbonyl, alkylthio, aminoalkyl, cyanoalkyl, aryl and the like. In other representative embodiments of the invention, $A_2$ is substituted or unsubstituted pyridyl.

In representative embodiments of the invention, the compounds of the invention include, for example, 4-{2-[(4-bromophenyl)amino]quinazolin-6-yloxy}-(2-pyridyl)-N-methylcarboxamide, N-methyl-4-{[2-({4-[(trifluoromethyl)oxy]phenyl}amino)-quinazolin-6-yl]oxy}pyridine-2-carboxamide, N-methyl-4-[(2-{[4-(trifluoromethyl)-phenyl]amino}quinazolin-6-yl)oxy]pyridine-2-carboxamide, 4-[(2-{[2-fluoro-5-(tri-fluoromethyl)phenyl]amino}quinazolin-6- yl)oxy]-N-methylpyridine-2-carboxamide, N-methyl-4-[(2-{[3-(trifluoromethyl)phenyl]amino}quinazolin-6-yl)oxy]pyridine-2-carboxamide, 4-({2-[(4-bromo-3-methylphenyl)amino]quinazolin-6-yl}oxy)-N-methyl-pyridine-2-carboxamide, 4-[(2-{[4-fluoro-3-(trifluoromethyl)phenyl]amino}quinazolin-6-yl)oxy]-N-methylpyridine-2-carboxamide, N-methyl-4-[(2-{[4-(methylthio)phenyl]amino}quinazolin-6-yl)oxy]pyridine-2-carboxamide, N-methyl-4-{[2-({4-[(phenyl-methyl)oxy]phenyl}amino)quinazolin-6-yl]oxy}pyridine-2-carboxamide, N-methyl-4-({2-[(4-morpholin-4-ylphenyl)amino]quinazolin-6-yl}oxy)pyridine-2-carboxamide, 4-({2-[(6-chloropyridin-3-yl)amino]quinazolin-6-yl}oxy)-N-methylpyridine-2-carboxamide, 4-[(2-{[4-chloro-3-(trifluoromethyl)phenyl]amino}quinazolin-6-yl)oxy]-N-methylpyridine-2-carboxamide, 4-({2-[(3,5-dichlorophenyl)amino]quinazolin-6-yl}oxy)-N-methylpyridine-2-carboxamide, N-methyl-4-[(2-{[6-(methyloxy)pyridin-3-yl]amino}-quinazolin-6-yl)oxy]pyridine-2-carboxamide, N-methyl-4-{[2-(phenylamino)quinazolin-6-yl]oxy}pyridine-2-carboxamide, 4-{[2-(bicyclo[2.2.1]hept-2-ylamino)quinazolin-6-yl]-oxy}-N-methylpyridine-2-carboxamide, 4-{[2-(cyclohexylamino)quinazolin-6-yl]oxy}-N-methylpyridine-2-carboxamide, N-methyl-4-({2-[(phenylmethyl)amino]quinazolin-6-yl}oxy)pyridine-2-carboxamide, N-methyl-4-({2-[(2-phenylethyl)amino]quinazolin-6-yl}oxy)pyridine-2-carboxamide, 4-[(2-{[(1-ethylpyrrolidin-2-yl)methyl]amino}quinazolin-6-yl)oxy]-N-methylpyridine-2-carboxamide, 4-[(2-{[2-bromo-4-(1-methyl-ethyl)phenyl]amino}quinazolin-6-yl)oxy]-N-methylpyridine-2-carboxamide, 4-({2-[(4-bromo-2-fluorophenyl)amino]quinazolin-6-yl}oxy)-N-methylpyridine-2-carboxamide, N-methyl[4-(2-methylsulfonylquinazolin-6-yloxy)(2-pyridyl)]carboxamide, N-methyl-4-{[2-({4-[(trifluoromethyl)oxy]phenyl}amino)quinazolin-6-yl]oxy}pyridine-2-carboxamide, N-methyl-4-[(2-{[4-(trifluoromethyl)phenyl]amino}quinazolin-6-yl)oxy]pyridine-2-carboxamide, 4-[(2-{[2-fluoro-5-(trifluoromethyl)phenyl]amino}-quinazolin-6-yl)oxy]-N-methylpyridine-2-carboxamide, N-methyl-4-[(2-{[3-(trifluoromethyl)phenyl]amino}quinazolin-6-yl)oxy]pyridine-2-carboxamide, 4-({2-[(4-bromo-3-methylphenyl)amino]quinazolin-6-yl}oxy)-N-methylpyridine-2-carboxamide, 4-[(2-{[4-fluoro-3-(trifluoromethyl)phenyl]amino}quinazolin-6-yl)oxy]-N-methylpyridine-2-carboxamide, N-methyl-4-[(2-{[4-(methylthio)phenyl]amino}quinazolin-6-yl)oxy]-pyridine-2-carboxamide, N-methyl-4-{[2-({4-[(phenylmethyl)oxy]phenyl}amino)-quinazolin-6-yl]oxy}pyridine-2-carboxamide, N-methyl-4-({2-[(4-morpholin-4-yl-phenyl)amino]quinazolin-6-yl}oxy)pyridine-2-carboxamide, 4-({2-[(6-chloropyridin-3-yl)amino]quinazolin-6-yl}oxy)-N-methylpyridine-2-carboxamide, 4-[(2-{[4-chloro-3-(trifluoromethyl)phenyl]amino}quinazolin-6-yl)oxy]-N-methylpyridine-2-carboxamide, 4-({2-[(3,5-dichlorophenyl)amino]quinazolin-6-yl}oxy)-N-methylpyridine-2-carboxamide, N-methyl-4-[(2-{[6-(methyloxy)pyridin-3-yl]amino}quinazolin-6-yl)oxy]-pyridine-2-carboxamide, N-methyl-4-{[2-(phenylamino)quinazolin-6-yl]oxy}pyridine-2-carboxamide, 4-{[2-(bicyclo[2.2.1]hept-2-ylamino)quinazolin-6-yl]oxy}-N-methyl-pyridine-2-carboxamide, 4-{[2-(cyclohexylamino)quinazolin-6-yl]oxy}-N-methyl-pyridine-2-carboxamide, N-methyl-4-({2-[(phenylmethyl)amino]quinazolin-6-yl}oxy)-pyridine-2-carboxamide, N-methyl-4-({2-[(2-phenylethyl)amino]quinazolin-6-yl}oxy)-pyridine-2-carboxamide, 4-[(2-{[(1-ethylpyrrolidin-2-yl)methyl]amino}quinazolin-6-yl)-oxy]-N-methylpyridine-2-carboxamide, 4-[(2-{[2-bromo-4-(1-methylethyl)phenyl]-amino}quinazolin-6-yl)oxy]-N-methylpyridine-2-carboxamide, 4-({2-[(4-bromo-2-fluorophenyl)amino]quinazolin-6-yl}oxy)-N-methylpyridine-2-carboxamide, 4-({2-[(2,4-dichlorophenyl)amino]quinazolin-6-yl}oxy)-N-methylpyridine-2-carboxamide, 4-{[2-(isoquinolin-1-ylamino)quinazolin-6-yl]oxy}-N-methylpyridine-2-carboxamide, 4-({2-[(2-bromophenyl)amino]quinazolin-6-yl}oxy)-N-methylpyridine-2-carboxamide, 4-({2-[(2-ethylphenyl)amino]quinazolin-6-yl}oxy)-N-methylpyridine-2-carboxamide, 4-({2-[(3-fluoro-2-methylphenyl)amino]quinazolin-6-yl}oxy)-N-methylpyridine-2-carboxamide, N-methyl-4-[(2-{[2-(phenyloxy)phenyl]amino}quinazolin-6-yl)oxy]-pyridine-2-carboxamide, N-methyl-4-{[2-(quinolin-2-ylamino)quinazolin-6-yl]oxy}-pyridine-2-carboxamide, 4-({2-[(2,5-dimethylphenyl)amino]quinazolin-6-yl}oxy)-N-methylpyridine-2-carboxamide, N-methyl-4-[(2-{[5-methyl-2-(methyloxy)phenyl]-amino}quinazolin-6-yl)oxy]pyridine-2-carboxamide, N-methyl-4-{[2-(pyridin-2-yl-amino)quinazolin-6-yl]oxy}pyridine-2-carboxamide, N-methyl-4-({2-[(2-morpholin-4-yl-phenyl)amino]quinazolin-6-yl}oxy)pyridine-2-carboxamide, N-methyl-4-[(2-{[2-(methyloxy)-5-(trifluoromethyl)phenyl]amino}quinazolin-6-yl)oxy]pyridine-2-carboxamide, 4-({2-[(3-fluorophenyl)amino]quinazolin-6-yl}oxy)-N-methylpyridine-2-carboxamide, 4-({2-[(3-chlorophenyl)amino]quinazolin-6-yl}oxy)-N-methylpyridine-2-carboxamide, 4-({2-[(3-bromophenyl)amino]quinazolin-6-yl}oxy)-N-methylpyridine-2-carboxamide, 4-{[2-(2,3-dihydro-1,4-benzodioxin-6-ylamino)quinazolin-6-yl]oxy}-N-methylpyridine-2-carboxamide, 4-[(2-{[3,5-bis(trifluoromethyl)phenyl]amino}-quinazolin-6-yl)oxy]-N-methylpyridine-2-carboxamide, 4-[(2-{[3-chloro-4-(methyloxy)-phenyl]amino}quinazolin-6-yl)oxy]-N-methylpyridine-2-carboxamide, N-methyl-4-[(2-{[3-(methylthio)phenyl]amino}quinazolin-6-yl)oxy]pyridine-2-carboxamide, N-methyl-4-{[2-(pyridin-3-ylamino)quinazolin-6-yl]oxy}pyridine-2-carboxamide, N-methyl-4-{[2-({3-[(phenylmethyl)oxy]phenyl}amino)quinazolin-6-yl]oxy}pyridine-2-carboxamide, 4-{[2-(1,1'-biphenyl-3-ylamino)quinazolin-6-yl]oxy}-N-methylpyridine-2-carboxamide, N-methyl-4-{[2-({3-[(trifluoromethyl)oxy]phenyl}amino)quinazolin-6-yl]oxy}pyridine-2-carboxamide, 4-({2-[(3-ethynylphenyl)amino]quinazolin-6-yl}oxy)-N-methylpyridine-2-carboxamide, 4-({2-[(3,4-difluorophenyl)amino]quinazolin-6-yl}oxy)-N-methylpyridine-2-carboxamide, 4-({2-[(3,4-dimethylphenyl)amino]quinazolin-6-yl}-oxy)-N-methylpyridine-2-carboxamide, N-methyl-4-({2-[(4-piperidin-1-ylphenyl)-amino]quinazolin-6-yl}oxy)pyridine-2-carboxamide, N-methyl-4-[(2-{[4-(methyloxy)-phenyl]amino}quinazolin-6-yl)oxy]pyridine-2-carboxamide, 4-({2-[(4-ethylphenyl)-amino]quinazolin-6-yl}oxy)-N-methylpyridine-2-carboxamide, 4-[(2-{[4-(butyloxy)-phenyl]amino}quinazolin-6-yl)oxy]-N-methylpyridine-2-carboxamide, N-methyl-4-[(2-{[4-(1-methylethyl)phenyl]amino}quinazolin-6-yl)oxy]pyridine-2-carboxamide, 4-[(2-{[5-chloro-2-(methyloxy)phenyl]amino}quinazolin-6-yl)oxy]-N-methylpyridine-2-carboxamide, 4-[(2-{[5-cyclohexyl-2-(methyloxy)phenyl]amino}quinazolin-6-yl)oxy]-N-methylpyridine-2-carboxamide, N-methyl-4-({2-[(4-methyl-1,1'-biphenyl-3-yl)amino]-quinazolin-6-yl}oxy)pyridine-2-carboxamide, 4-{[2-(2,3-dihydro-1H-inden-5-ylamino)-quinazolin-6-yl]oxy}-N-methylpyridine-2-carboxamide, 4-{[2-(1,1'-biphenyl-4-ylamino)-quinazolin-6-yl]oxy}-N-methylpyridine-2-carboxamide, 4-({2-[(4-fluorophenyl)amino]-quinazolin-6-yl}oxy)-N- methylpyridine-2-carboxamide, 4-({2-[(2,3-difluorophenyl)-amino]quinazolin-6-yl}oxy)-N-methylpyridine-2-carboxamide, 4-({2-[(2,2-difluoro-1,3-benzodioxol-5-yl)amino]quinazolin-6-yl}oxy)-N-methylpyridine-2-carboxamide, 4-{[2-(9H-fluoren-2-ylamino)quinazolin-6-yl]oxy}-N-methylpyridine-2-carboxamide, 4-({2-[(3-cyclohexylphenyl)amino]quinazolin-6-yl}oxy)-N-methylpyridine-2-carboxamide, N-methyl-4-[(2-{[3-(1-methylethyl)phenyl]amino}quinazolin-6-yl)oxy]pyridine-2-carboxamide, 4-({2-[(4-bromophenyl)amino]quinazolin-6-yl}oxy)-N-[3-(2-oxo-pyrrolidin-1-yl)propyl]pyridine-2-carboxamide, 4-({2-[(4-bromophenyl)amino]-quinazolin-6-yl}oxy)-N-(2-hydroxyethyl)pyridine-2-carboxamide, 4-({2-[(4-bromophenyl)amino]quinazolin-6-yl}oxy)-N-[3-(1H-imidazol-1-yl)propyl]pyridine-2-carboxamide, 4-({2-[(4-bromophenyl)amino]quinazolin-6-yl}oxy)-N-[3-(methyloxy)propyl]-pyridine-2-carboxamide, 4-({2-[(4-bromophenyl)amino]quinazolin-6-yl}oxy)-N-(2-piperidin-1-ylethyl)pyridine-2-carboxamide, 4-({2-[(4-bromophenyl)amino]-quinazolin-6-yl}oxy)-N-propylpyridine-2-carboxamide, 4-({2-[(4-bromophenyl)amino]-quinazolin-6-yl}oxy)-N-[2-(dimethylamino)ethyl]pyridine-2-carboxamide, N-methyl-4-{[2-({3-[(trifluoromethyl)thio]phenyl}amino)quinazolin-6-yl]oxy}pyridine-2-carboxamide, 4-({2-[(4-chloro-2-fluorophenyl)amino]quinazolin-6-yl}oxy)-N-methylpyridine-2-carboxamide, 4-({2-[(4-chloro-3-methylphenyl)amino]quinazolin-6-yl}oxy)-N-methyl-pyridine-2-carboxamide, 4-({2-[(4-butylphenyl)amino]quinazolin-6-yl}oxy)-N-methyl-pyridine-2-carboxamide, (4-{2-[(4-bromo-3-methylphenyl)amino](6-quinolyloxy)}-(2-pyridyl))-N-methylcarboxamide, and N-methyl-4-[(2-{[3-(1-methylethyl)phenyl]-amino}quinolin-6-yl)oxy]pyridine-2-carboxamide, and other representative compounds set forth in the Examples.

In other aspects, the present invention relates to the processes for preparing the compounds of Formulas I-VIII and to the synthetic intermediates useful in such processes.

The compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, as well as single diastereomers of the compounds of the invention are included in the present invention. The terms "S" and "R" configuration, as used herein, are as defined by the IUPAC 1974 RECOMMENDATIONS FOR SECTION E, FUNDAMENTAL STEREOCHEMISTRY, Pure Appl. Chem. 45:13-30 (1976). The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the CHEMICAL ABSTRACTS INDEX GUIDE-APPENDIX IV (1987) paragraph 203.

The present invention also relates to the processes for preparing the compounds of the invention and to the synthetic intermediates useful in such processes, as described in detail below.

Synthetic Methods

Compounds of the invention containing a quinazoline or quinoline core may be prepared using a number of methods familiar to one of skill in the art. In one method, compounds of the invention may be produced from the intermediate 2-chloro-6-methoxyquinazoline 8, which may be obtained as described in the following scheme and in Example 1, below.

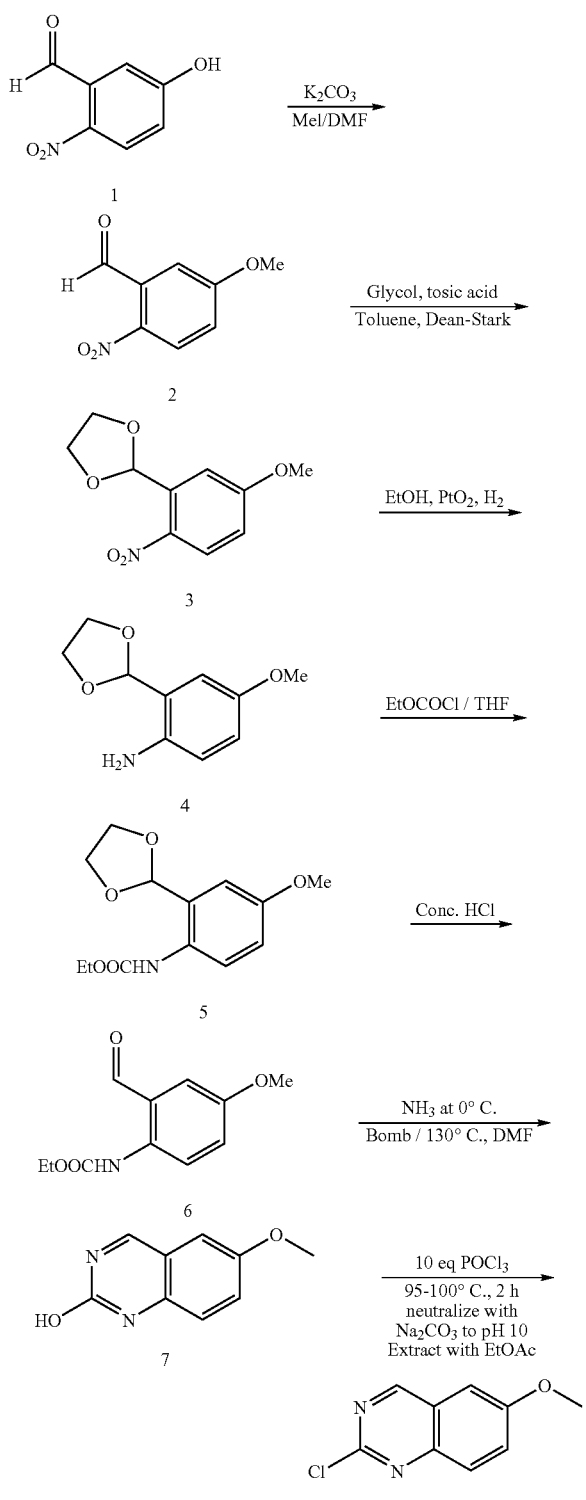

In this scheme 5-hydroxy-2-nitrobenzaldehyde 1 is reacted in DMF with iodomethane and potassium carbonate to yield 5-methoxy-2-nitrobenzaldehyde 2. The methoxybenzaldehyde is heated with p-toluene sulfonic acid monohydrate (catalytic amount) in toluene to obtain the dioxane derivative 3, which is hydrogenated to give 2-(1,3-dioxolan-2yl)-4-methoxyphenylamine 4. Following conversion to the ethoxycarboxamide 5 and then to the formyl carboxamide 6, 6-methoxyquinazolin-2-ol 7 is obtained by ring closure with ammonia. Reaction with phosphorus oxychloride then yields the desired 2-chloro-6-methoxyquinazoline intermediate 8.

Scheme A:

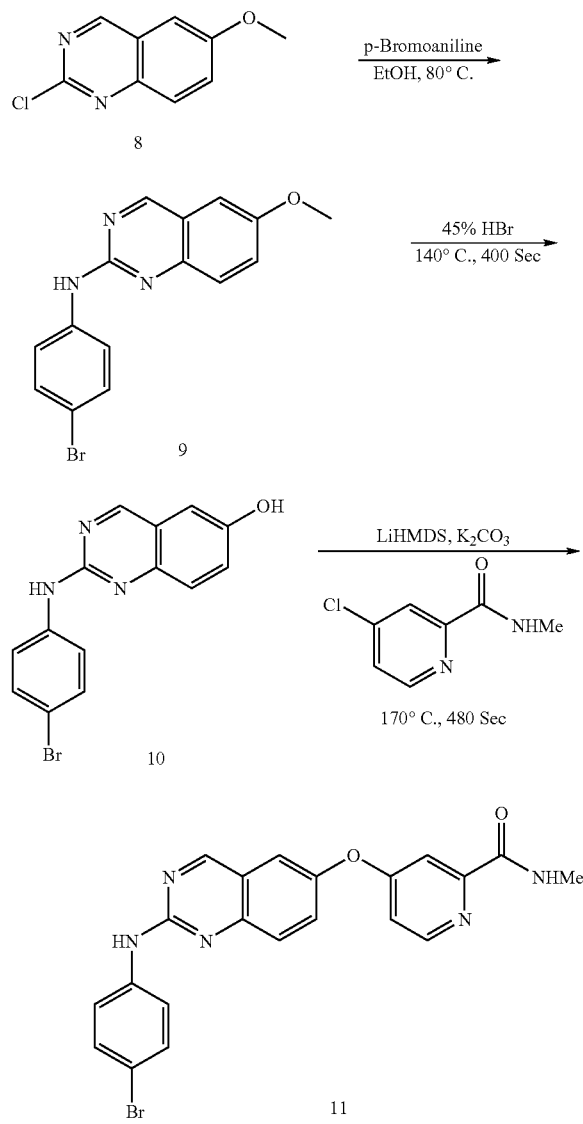

Scheme B:

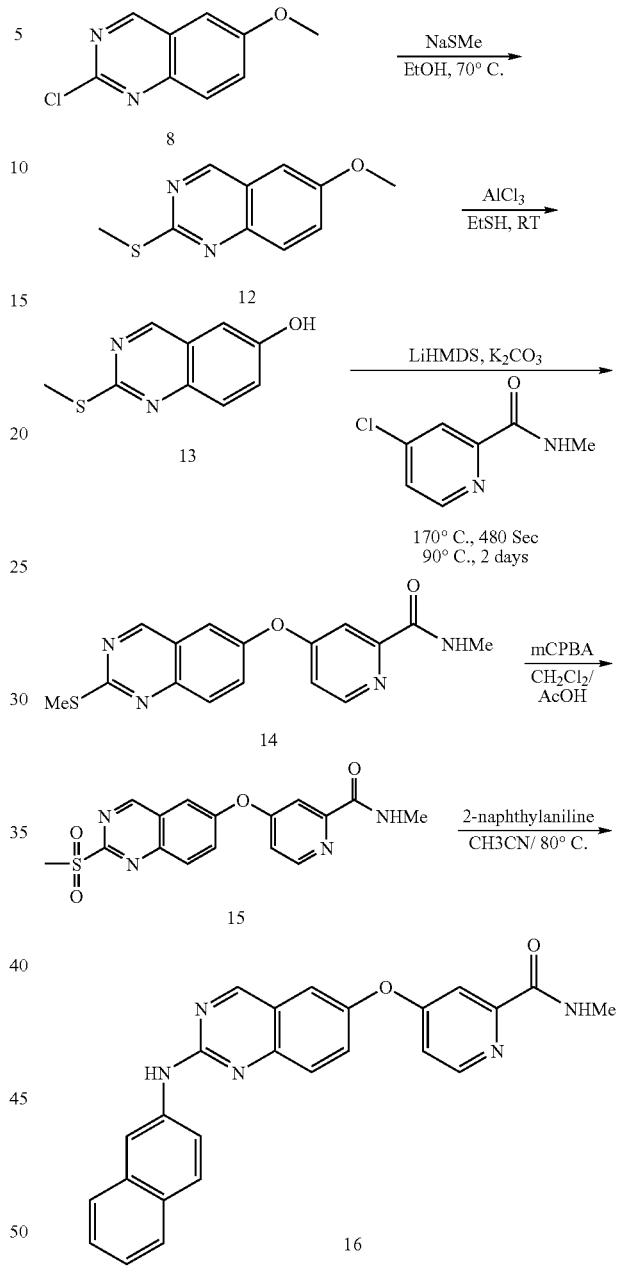

Referring to reaction scheme A, above, representative compounds of the invention may be obtained by reacting 6-methoxyquinazolin-2-ol 8 and with an arylamine, such as 4-bromoaniline, to obtain the corresponding arylmethoxyquinazoline 9, which may be heated to obtain the corresponding alcohol 10. The desired substituent, such as 4-chloro(2-pyridyl)-N-methylcarboxamide, is then added to the alcohol group to obtain the desired compound of the invention, in this case 4-{2-[(4-bromophenyl)amino]-quinazolin-6-yloxy}-(2-pyridyl)-N-methylcarboxamide 11.

In the alternate reaction Scheme B, above, the 2-chloro-6-methoxyquinazoline 8 is reacted with sodium thiomethoxide in ethanol, dry methylene chloride, ethane thiol and aluminum chloride to obtain the 2-methylthioquinazolin-6-ol 13. The desired substituent, in this case 4-chloro(2-pyridyl)-N-methylcarboxamide, is added to the alcohol group to obtain the corresponding substituted methylthioquinazoline 14. Treatment with 3-chloroperoxybenzoic acid in acetic acid results in the corresponding sulfonyl 15, which is replaced by a desired substituent, in this case 2-naphthylaniline, to obtain the desired compound of the invention, in this case N-methyl-4-{[2-(naphthalen-2-ylamino)-quinazolin-6-yl]oxy}pyridine-2-carboxamide.

Quinoline compounds of the invention can be similarly synthesized, such as in the following reaction Scheme C:

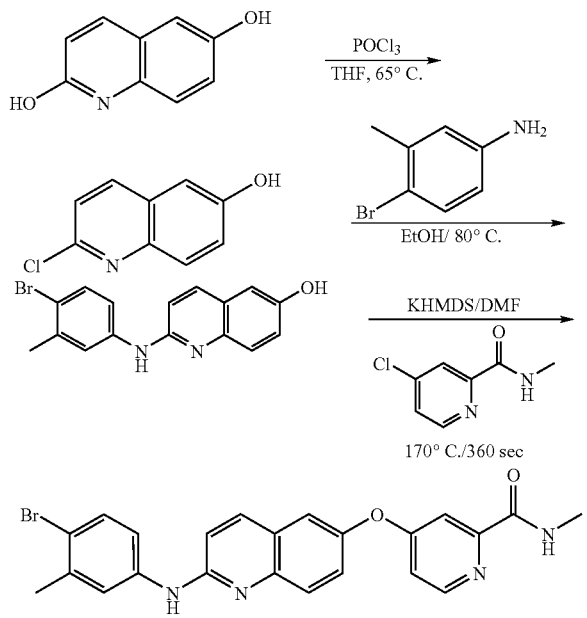

As set forth in reaction Scheme C, quinoline2,6-diol is chlorinated with POCl₃ to obtain 2-chloroquinolin-6-ol, which is reacted with a desired amine substituent, in this case 4-bromo-3-methylaniline, and to obtain the amine substituted quinolinol. A mixture of the alcohol and potassium bis(trimethylsilyl)amide in dimethylformamide is reacted with a desired substituent at the alcohol group, in this case dimethylformamide, to obtain the desire product, in this case (4-{2-[(4-bromo-3-methylphenyl)amino](6-quinolyloxy)}(2-pyridyl))-N-methylcarboxamide.

Compounds of the invention wherein Y=O or S may generally be prepared as shown in examples 1-92 below. Compounds containing Y=C may generally be prepared as described in WO 03/031458. Compounds having Y=N may generally be prepared by treating hydroxy-substituted quinolinyl, isoquinolinyl, or quinazolinyl compounds with triflic anhydride followed by the appropriate aryl or heteroaryl amines under Pd catalyzed conditions (Old, D. W.; Wolfe, J. P.; Buchwald, S. L. *J. Am. Chem. Soc.* 1998, 120, 9722-9723).

Various other compounds of the invention can be made by treating an appropriately functionalized heteroaryl or aryl acid (-A₂-COOH) with sodium azide or diphenylphosphoryl azide under Schmidt/Curtius rearrangement conditions to form the corresponding heteroarylisocyanate (-A₂-N=C=O) intermediates. These isocyanates need not be isolated and may be readily converted via known procedures to amines, amides, thioamides, carbamates, thiocarbamates, ureas, and thioureas.

The compounds of the invention are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinyl-pyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Effective amounts of the compounds of the invention generally include any amount sufficient to detectably inhibit Raf activity by any of the assays described herein, by other Raf kinase activity assays known to those having ordinary skill in the art or by detecting an inhibition or alleviation of symptoms of cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose.

The compounds of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq. (1976).

While the compounds of the invention can be administered as the sole active pharmaceutical agent, they can also be used in combination with one or more other agents used in the treatment of cancer. Representative agents useful in combination with the compounds of the invention for the treatment of cancer include, for example, irinotecan, topotecan, gemcitabine, 5-fluorouracil, leucovorin carboplatin, cisplatin, taxanes, tezacitabine, cyclophosphamide, vinca alkaloids, imatinib (Gleevec), anthracyclines, rituximab, trastuzumab, dacarbazine, aldesleukin, capecitabine, and Iressa (gefitinib), as well as other cancer chemotherapeutic agents.

The above compounds to be employed in combination with the compounds of the invention will be used in therapeutic amounts as indicated in the *Physicians' Desk Reference* (PDR) 47th Edition (1993), which is incorporated herein by reference, or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

Antiestrogens, such as tamoxifen, inhibit breast cancer growth through induction of cell cycle arrest, that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to antiestrogen resistance (Donovan et al, *J. Biol. Chem.* 276:40888, 2001). As reported by Donovan et al., inhibition of MAPK signaling through treatment with MEK inhibitor changed the phosphorylation status of p27 in hormone refactory breast cancer cell lines and in so doing restored hormone sensitivity. Accordingly, in one aspect, the compounds of formulas (I)-(V) may be used in the treatment of hormone dependent cancers, such as breast and prostate cancers, to reverse hormone resistance commonly seen in these cancers with conventional anticancer agents.

In hematological cancers, such as chronic myelogenous leukemia (CML), chromosomal translocation is responsible for the constitutively activated BCR-AB1 tyrosine kinase. The afflicted patients are responsive to Gleevec, a small molecule tyrosine kinase inhibitor, as a result of inhibition of Ab1 kinase activity. However, many patients with advanced stage disease respond to Gleevec initially, but then relapse later due to resistance-conferring mutations in the Ab1 kinase domain. In vitro studies have demonstrated that BCR-Av1 employs the Raf kinase pathway to elicit its effects. In addition, inhibiting more than one kinase in the same pathway provides additional protection against resistance-conferring mutations. Accordingly, in another aspect of the invention, the compounds of formulas (I)-(VIII) are used in combination with at least one additional agent, such as Gleevec, in the treatment of hematological cancers, such as chronic myelogenous leukemia (CML), to reverse or prevent resistance to the at least one additional agent.

The present invention will be understood more readily by reference to the following examples, which are provided by way of illustration and are not intended to be limiting of the present invention.

Representative side chains for use in the compounds of the following examples may generally be prepared in accordance with the following procedures:

Example 1

Synthesis of (4-{2-[(4-bromophenyl)amino]quinazolin-6-yloxy}-(2-pyridyl))-N-methylcarboxamide

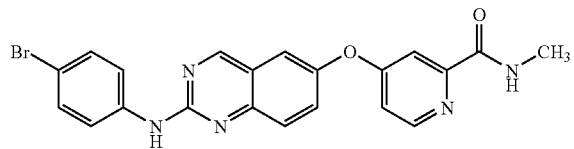

The compound (4-{2-[(4-bromophenyl)amino]quinazolin-6-yloxy}-(2-pyridyl))-N-methylcarboxamide was synthesized as follows:

Step 1. Synthesis of 5-methoxy-2-nitrobenzaldehyde 2

A mixture containing 5-hydroxy-2-nitrobenzaldehyde (1 eq) in DMF with iodomethane (1.1eq) and potassium carbonate (1eq) was stirred at room temperature for 16 hours. The resulting mixture was concentrated and partitioned between ethyl acetate and water. The organic layer was washed with brine and dried and concentrated to afford 5-methoxy-2-nitrobenzaldehyde in quantitative yield.
MS: MH+=182.

Step 2. Synthesis of 2-(1,3-dioxolan-2-yl)-4-methoxy-1-nitrobenzene 3

The mixture 5-methoxy-2-nitrobenzaldehyde (1 eq), ethylene glycol (1.4eq) and p-toluene sulfonic acid monohydrate (catalytic amount) in toluene was heated to reflux with a Dean-Stark apparatus for 16 hours. The mixture was then concentrated and passed through a plug of silica to give 2-(1, 3-dioxolan-2-yl)-4-methoxy-1-nitrobenzene in 85-90% yield.
MS: MH+=226.

Step 3. Synthesis of 2-(1,3-dioxolan-2-yl)-4-methoxyphenylamine 4

A solution of 2-(1,3-dioxolan-2-yl)-4-methoxy-1-nitrobenzene (1eq) in ethyl acetate was treated with sodium acetate (0.08eq) and platinum oxide (0.06eq) and hydrogenated in a Parr apparatus at 50 psi for 16 hours. The reaction mixture was filtered and the filtrate was concentrated to give 2-(1,3-dioxolan-2yl)-4-methoxyphenylamine in quantitative yield.
MS: MH+=196.

Step 4. Synthesis of N-(2-(1,3-dioxolan-2-yl)-4-methoxyphenyl)ethoxy-carboxamide 5

Ethyl chloroformate (1.2 eq) was added to 2-(1,3-dioxolan-2-yl)-4-methoxyphenylamine (1eq) and triethyl amine (1.2 eq) in THF at 0° C. The reaction was completed instantaneously. The mixture was concentrated and partitioned between ethyl acetate and water. The organic layer was washed with brine and dried and concentrated to give N-(2-(1,3-dioxolan-2-yl)-4-methoxyphenyl)ethoxycarboxamide as a yellow solid in quantitative yield.
MS: MH+=268.

Step 5. Synthesis of Ethoxy-N-(2-formyl-4-methoxyphenyl) carboxamide 6

N-(2-(1,3-dioxolan-2-yl)-4-methoxyphenyl)ethoxycarboxamide was dissolved in acetone and to it was added hydrochloric acid. The mixture was stirred at room temperature for 4 hours. The solvent was removed in vacuo to give ethoxy-N-(2-formyl-4-methoxyphenyl)carboxamide quantitatively.
MS: MH+=224

Step 6. Synthesis of 6-methoxyquinazolin-2-ol 7

Ammonia was bubbled into ethanol cooled to dry ice bath temperature for 1 hour. Ethoxy-N-(2-formyl-4-methoxyphenyl)carboxamide was added and the resultant solution was heated to 130° C. in an autoclave for 16 hours. The brown solution was treated with charcoal, filtered and the filtrate was concentrated. A yellow was subjected to chromatography to give 6-methoxyquinazolin-2-ol.
MS: MH+=177

Step 7. Synthesis of 2-chloro-6-methoxyquinazoline 8

6-methoxyquinazolin-2-ol (1eq) and phosphorus oxychloride (2-10eq) was refluxed for 2 hours. The reaction mixture was concentrated and neutralized with sodium carbonate, which was then filtered off. The concentrate was partitioned between ethyl acetate and water. The organic layer was washed with brine dried and concentrated. The crude was subjected to column chromatography (10% Acetone in hexane) to afford 2-chloro-6-methoxyquinazoline as a beige color solid in 90% yield.
MS: MH+=195.

Step 8. Synthesis of (4-bromophenyl)(6-methoxyquinazolin-2-yl)amine 9

2-chloro-6-methoxyquinazoline (1eq) and 4-bromoaniline (2 eq) in ethanol was heated at 80° C. for 16 h. The mixture was concentrated and passed through a plug of silica to yield (4-bromophenyl)(6-methoxyquinazolin-2-yl)amine.
MS: MH+=330.

Step 9. Synthesis of 2-[(4-bromophenyl)amino]quinazolin-6-ol 10

(4-bromophenyl)(6-methoxyquinazolin-2-yl)amine in HBr was heated at 100° C. for 16 hours. The reaction mixture was concentrated and purified on preparative chromatography. Lyophillization yielded 2-[(4-bromophenyl)amino]quinazolin-6-ol.
MS: MH+=316.

Step 10. Synthesis of (4-{2-[(4-bromophenyl)amino]quinazolin-6-yloxy}-(2-pyridyl))-N-methylcarboxamide The mixture containing 2-[(4-bromophenyl)amino]quinazolin-6-ol (1 eq), potassiumbis(trimethylsilyl)amide (4eq) was stirred in dimethylformamide for 10 min at room temperature. To this mixture was added (4-chloro(2-pyridyl)-N-methylcarboxamide (1 eq) and Potassium carbonate (1.2 eq) and microwaved for 6 mins at 170° C. The reaction mixture was then concentrated and partitioned between ethyl acetate and water. The organic layer was separated and washed with brine, dried, filtered and concentrated. Purification on preparative chromatography yielded 4-{2-[(4-bromophenyl)amino]quinazolin-6-yloxy}-(2-pyridyl)-N-methylcarboxamide in 70-75% yield.
MS: MH+=450.

Examples 2-108

The compounds shown in the following Table 1 (Examples 2-16) were prepared by following the procedure described for Example 1.

TABLE 1

| Example | Structure | Name | MH+ |
|---|---|---|---|
| 2 | 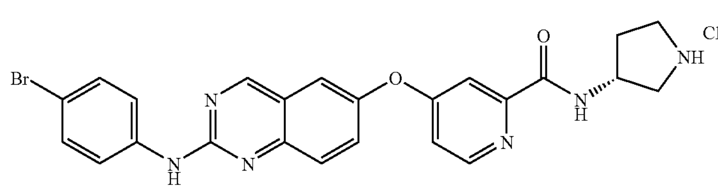 | 4-({2-[(4-bromophenyl)amino]-quinazolin-6-yl}oxy)-N-[(3R)-pyrrolidin-3-yl]pyridine-2-carboxamide | 506.4 |

TABLE 1-continued

| Example | Structure | Name | MH+ |
|---|---|---|---|
| 3 | 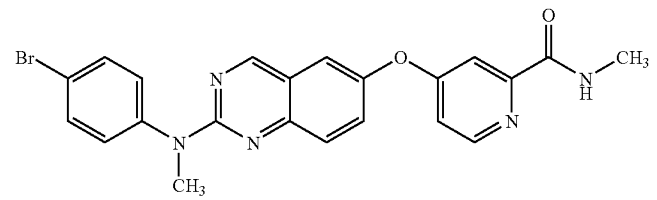 | 4-({2-[(4-bromophenyl)(methyl)-amino]quinazolin-6-yl}oxy)-N-methylpyridine-2-carboxamide | 465.3 |
| 4 | 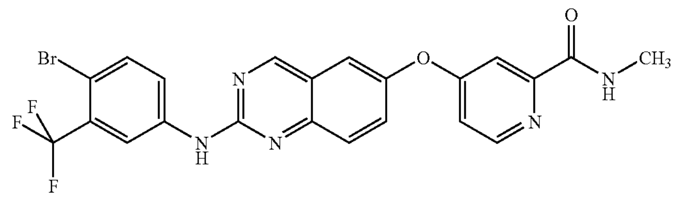 | 4-[(2-{[4-bromo-3-(trifluoro-methyl)phenyl]amino}quinazolin-6-yl)oxy]-N-methylpyridine-2-carboxamide | 519.3 |
| 5 | 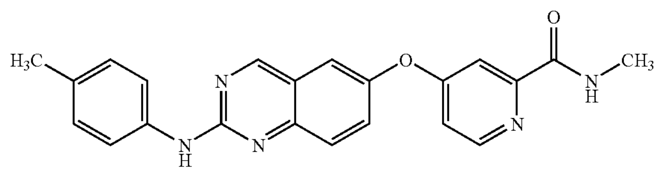 | N-methyl-4-({2-[(4-methylphenyl)-amino]quinazolin-6-yl}oxy)-pyridine-2-carboxamide | 386.4 |
| 6 | 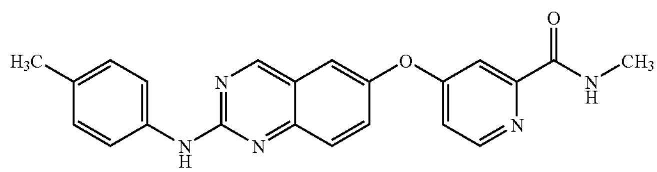 | N-methyl-4-[(2-{[4-(phenyloxy)phenyl]amino}quinazolin-6-yl)oxy]pyridine-2-carboxamide | 464.5 |
| 7 | 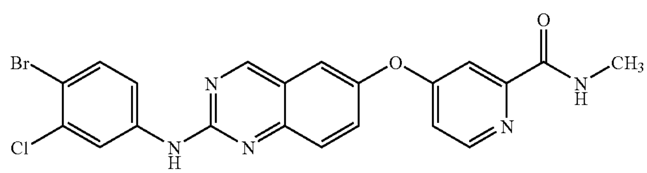 | 4-({2-[(4-bromo-3-chlorophenyl)amino]quinazolin-6-yl}oxy)-N-methylpyridine-2-carboxamide | 485.7 |
| 8 | 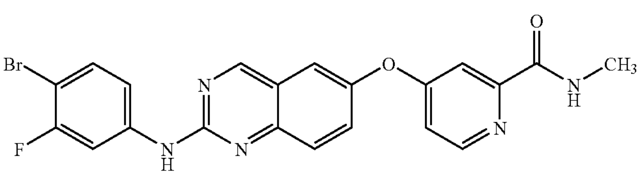 | 4-({2-[(4-bromo-3-fluorophenyl)-amino]quinazolin-6-yl}oxy)-N-methylpyridine-2-carboxamide | 469.3 |
| 9 | 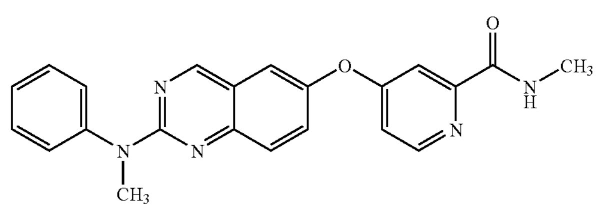 | N-methyl-4-({2-[methyl(phenyl)-amino]quinazolin-6-yl}oxy)-pyridine-2-carboxamide | 386.4 |
| 10 | 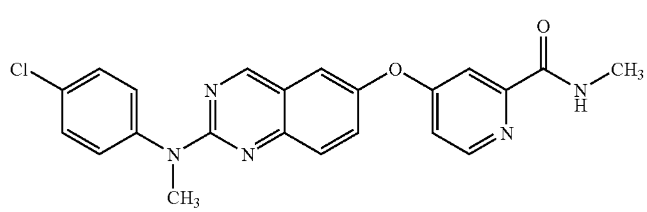 | 4-({2-[(4-chlorophenyl)(methyl)-amino]quinazolin-6-yl}oxy)-N-methylpyridine-2-carboxamide | 420.9 |

US 7,691,866 B2

TABLE 1-continued

| Example | Structure | Name | MH+ |
|---|---|---|---|
| 11 | 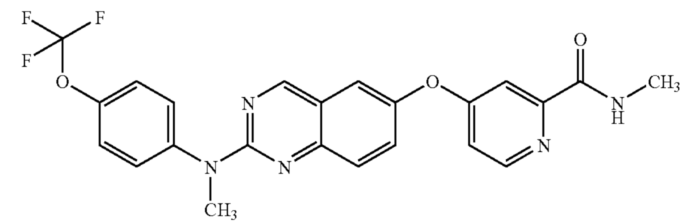 | N-methyl-4-{[2-(methyl{4-[(trifluoromethyl)oxy]phenyl}amino)quinazolin-6-yl]oxy}pyridine-2-carboxamide | 470.4 |
| 12 | 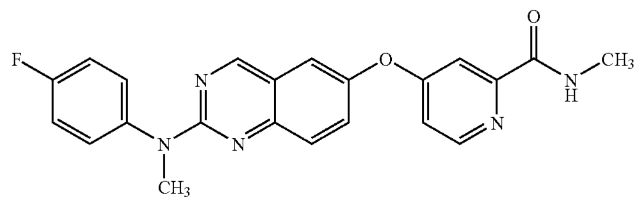 | 4-({2-[(4-fluorophenyl)(methyl)amino]quinazolin-6-yl}oxy)-N-methylpyridine-2-carboxamide | 404.4 |
| 13 | 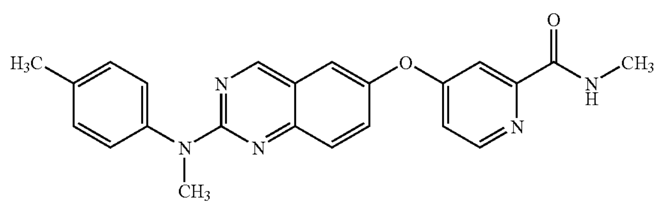 | N-methyl-4-({2-[methyl(4-methylphenyl)amino]quinazolin-6-yl}-oxy)pyridine-2-carboxamide | 400.5 |
| 14 | 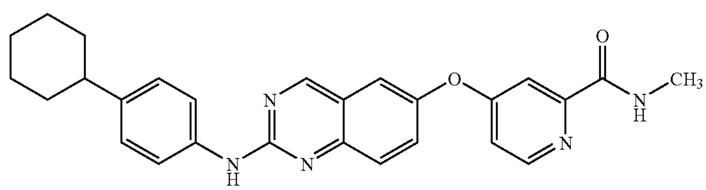 | 4-({2[(4-cyclohexylphenyl)-amino]quinazolin-6-yl}oxy)-N-methylpyridine-2-carboxamide | 454.5 |
| 15 | 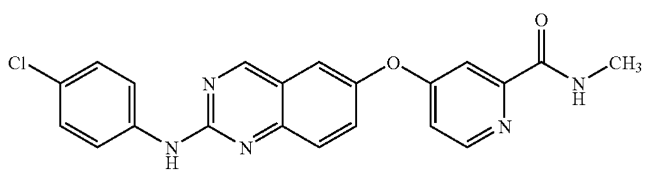 | 4-({2-[(4-chlorophenyl)amino]-quinazolin-6-yl}oxy)-N-methyl-pyridine-2-carboxamide | 406.8 |

Example 16

Synthesis of N-methyl-4-{[2-(naphthalen-2-ylamino)-quinazolin-6-yl]oxy}pyridine-2-carboxamide

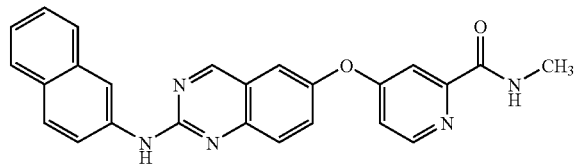

Step 1: Synthesis of N-methyl[4-(2-methylthio-quinazolin-6-yloxy)(2-pyridyl)]carboxamide 14

The mixture of 2-chloro-6-methoxyquinazoline (1 eq) and sodiumthiomethoxide (2 eq) in ethanol (0.5 M) was refluxed for 3 hours. The reaction was cooled down to room temperature and evaporated. The mixture was taken in ethyl acetate and washed with water and brine, dried in sodium sulfate and concentrated. The resulting crude was treated with dry methylene chloride and ethane thiol (5 eq) was added to it at room temperature. Aluminium chloride (5 eq) was added carefully at 0° C. The reaction was warmed to room temperature and stirred vigorously over night. The reaction was diluted with methylene chloride and saturated Rochelles's salt solution was added and stirred for about 3 hours until 2 layers separated. The organic layer was separated, washed with Rochelle's salt solution (2×), followed by water and brine, dried and evaporated. The crude 2-methylthioquinazolin-6-ol (1 eq) was taken in DMF (0.5 M) and Potassiumbis(trimethylsilyl)amide (2 eq) was added and stirred for 10 min at room temperature. 4-chloro(2-pyridyl)-N-methylcarboxamide (1.1 eq) was added followed by potassium carbonate (1 eq) and stirred at 85-90° C. for 16 hours. The mixture was diluted with ethyl acetate, washed with water and brine, dried and evaporated. The crude was subjected to column chromatography (4:1 Hexanes in ethyl acetate followed by 2:1 and 1:1 Hexanes in ethyl acetate) to afford the product in 75-85% yield.

Step 2. Synthesis of N-methyl[4-(2-methylsulfonylquinazolin-6-yloxy)(2-pyridyl)]carboxamide 15

The solution of N-methyl[4-(2-methylthioquinazolin-6-yloxy)(2-pyridyl)]-carboxamide in methylene chloride (0.5M) was treated with acetic acid (8-10%) and stirred for 5 min at room temperature. 3-chloroperoxybenzoic acid (2 eq) and after 2 hours another (1 eq) was added and stirred for 3 hours at room temperature. The reaction was diluted with methylene chloride and neutralized to pH8-9 with saturated sodium bicarbonate very carefully. The organic layer was separated, washed with water and brine to afford the product. The crude was subjected to column chromatography (1:1 hexanes in ethyl acetate) to afford the product quantitatively.

Step 3. Synthesis of N-methyl-4-{[2-(naphthalen-2-ylamino)-quinazolin-6-yl]oxy}pyridine-2-carboxamide N-methyl[4-(2-methylsulfonylquinazolin-6-yloxy)(2-pyridyl)]carboxamide 15 (1 eq) was treated with 2-naphthylaniline (2 eq) in acetonitrile (1 M) and heated at 80-85° C. The mixture was evaporated and purified on preparative chromatography to give the product.

Each of the Examples 17-119 shown in the following Table 2 were synthesized according to the procedure described in Example 109:

TABLE 2

| Example | Structure | Name | MH+ |
|---|---|---|---|
| 17 | 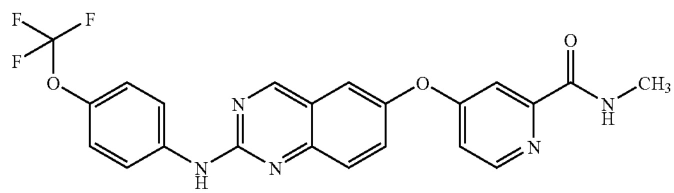 | N-methyl-4-{[2-({4-[(trifluoromethyl)oxy]phenyl}amino)-quinazolin-6-yl]oxy}pyridine-2-carboxamide | 456.4 |
| 18 | 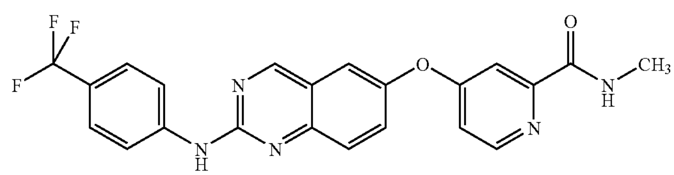 | N-methyl-4-[(2-{[4-(trifluoromethyl)phenyl]amino}quinazolin-6-yl)oxy]pyridine-2-carboxamide | 440.4 |
| 19 | 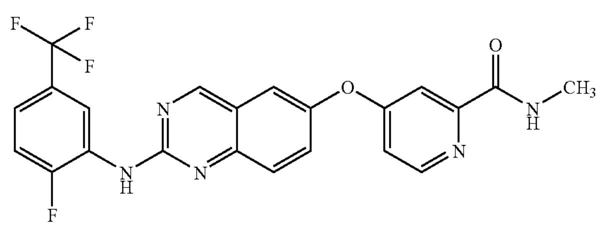 | 4-[(2-{[2-fluoro-5-(trifluoromethyl)phenyl]amino}quinazolin-6-yl)oxy]-N-methylpyridine-2-carboxamide | 458.4 |
| 20 | 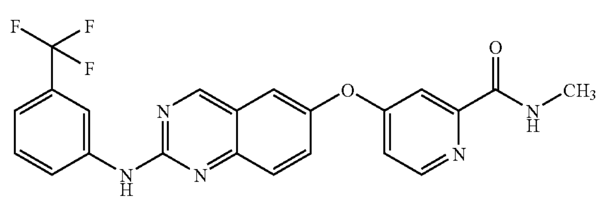 | N-methyl-4-[(2-{[3-(trifluoromethyl)phenyl]amino}quinazolin-6-yl)oxy]pyridine-2-carboxamide | 440.4 |
| 21 | 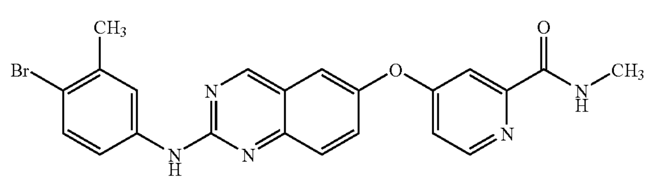 | 4-({2-[(4-bromo-3-methylphenyl)amino]quinazolin-6-yl}oxy)-N-methylpyridine-2-carboxamide | 465.3 |
| 22 | 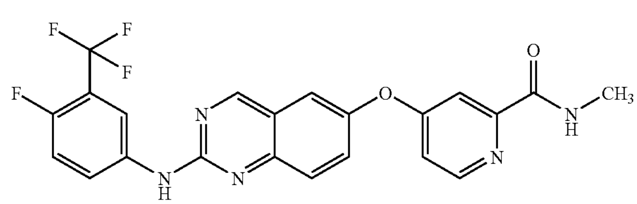 | 4-[(2-{[4-fluoro-3-(trifluoromethyl)phenyl]amino}quinazolin-6-yl)oxy]-N-methylpyridine-2-carboxamide | 458.4 |

TABLE 2-continued

| Example | Structure | Name | MH+ |
|---|---|---|---|
| 23 | 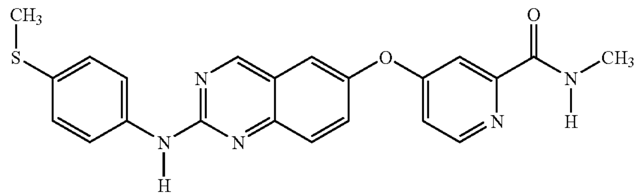 | N-methyl-4-[(2-{[4-(methylthio)phenyl]amino}quinazolin-6-yl)oxy]pyridine-2-carboxamide | 418.5 |
| 24 | 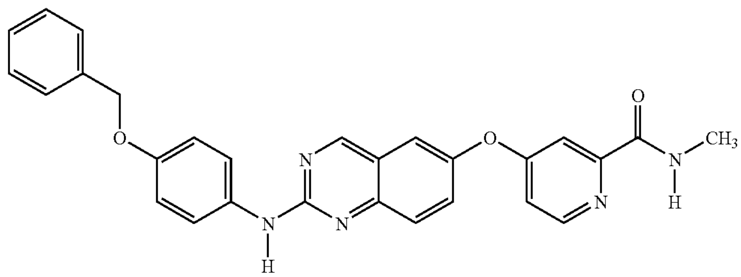 | N-methyl-4-{[2-({4-[(phenylmethyl)oxy]phenyl}amino)quinazolin-6-yl]oxy}pyridine-2-carboxamide | 478.5 |
| 25 | 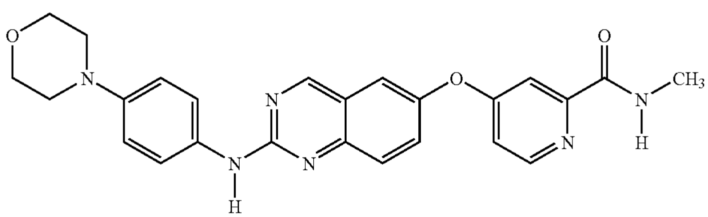 | N-methyl-4-({2-[(4-morpholin-4-ylphenyl)amino]quinazolin-6-yl}oxy)pyridine-2-carboxamide | 457.5 |
| 26 | 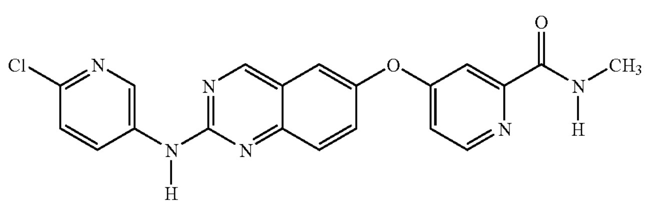 | 4-({2-[(6-chloropyridin-3-yl)amino]quinazolin-6-yl}oxy)-N-methylpyridine-2-carboxamide | 407.8 |
| 27 | 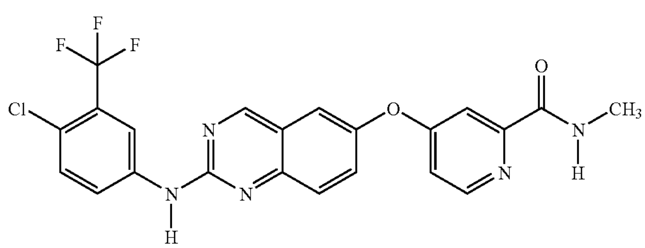 | 4-[(2-{[4-chloro-3-(trifluoromethyl)phenyl]amino}quinazolin-6-yl)oxy]-N-methylpyridine-2-carboxamide | 474.8 |
| 28 | 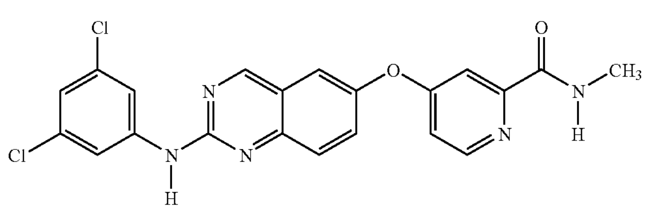 | 4-({2-[(3,5-dichlorophenyl)amino]quinazolin-6-yl}oxy)-N-methylpyridine-2-carboxamide | 441.3 |
| 29 | 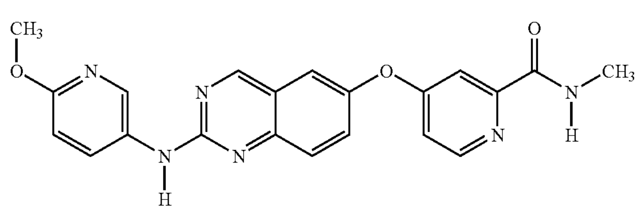 | N-methyl-4-[(2-{[6-(methyloxy)pyridin-3-yl]amino}quinazolin-6-yl)oxy]pyridine-2-carboxamide | 403.4 |

TABLE 2-continued

| Example | Structure | Name | MH+ |
| --- | --- | --- | --- |
| 30 | 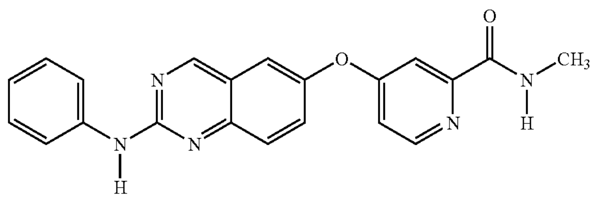 | N-methyl-4-{[2-(phenylamino)quinazolin-6-yl]oxy}pyridine-2-carboxamide | 372.4 |
| 31 | 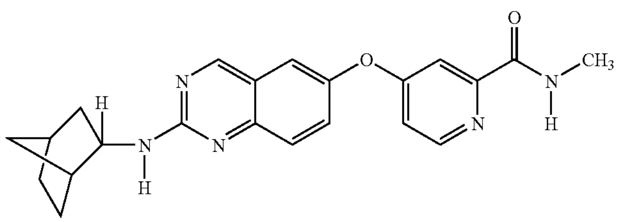 | 4-{[2-(bicyclo[2.2.1]hept-2-ylamino)quinazolin-6-yl]oxy}-N-methylpyridine-2-carboxamide | 390.5 |
| 32 | 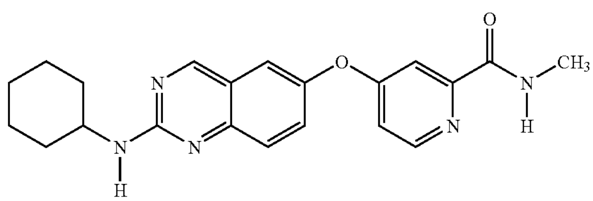 | 4-{[2-(cyclohexylamino)quinazolin-6-yl]oxy}-N-methylpyridine-2-carboxamide | 378.4 |
| 33 | 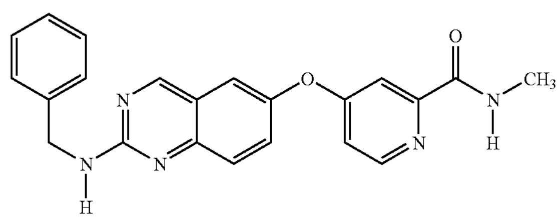 | N-methyl-4-({2-[(phenylmethyl)amino]quinazolin-6-yl}oxy)pyridine-2-carboxamide | 386.4 |
| 34 | 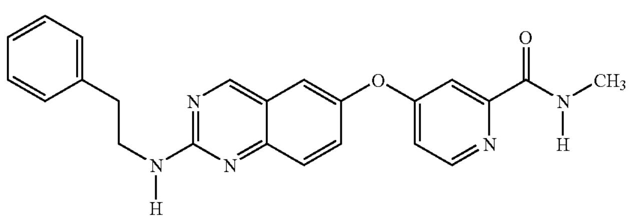 | N-methyl-4-({2-[(2-phenylethyl)amino]quinazolin-6-yl}oxy)pyridine-2-carboxamide | 400.5 |
| 35 | 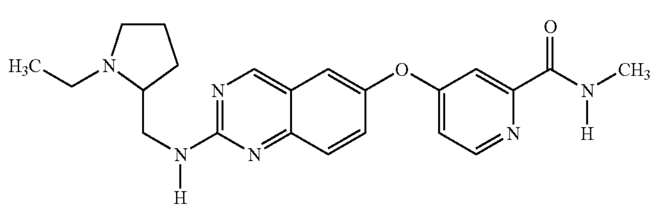 | 4-[(2-{[(1-ethylpyrrolidin-2-yl)methyl]amino}quinazolin-6-yl)oxy]-N-methylpyridine-2-carboxamide | 407.5 |
| 36 | 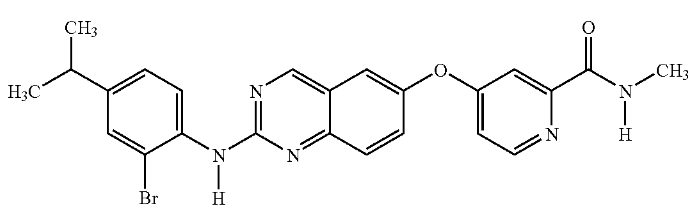 | 4-[(2-{[2-bromo-4-(1-methylethyl)phenyl]amino}quinazolin-6-yl)oxy]-N-methylpyridine-2-carboxamide | 493.4 |

TABLE 2-continued

| Example | Structure | Name | MH+ |
|---|---|---|---|
| 37 | 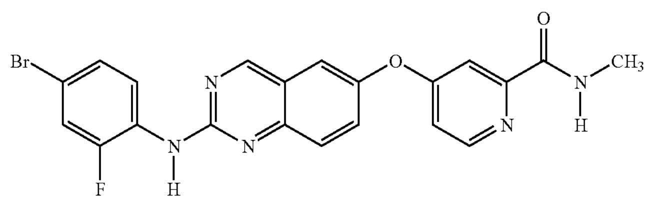 | 4-({2-[(4-bromo-2-fluorophenyl)amino]quinazolin-6-yl}oxy)-N-methylpyridine-2-carboxamide | 469.3 |

Examples 38-90

Additional Compounds

Following the foregoing general procedures, the following additional compounds were prepared:

TABLE 3

| Example | Structure | Name | MH+ |
|---|---|---|---|
| 38 | 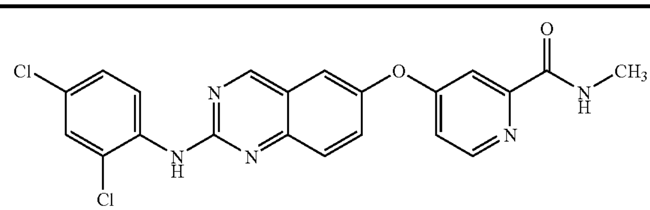 | 4-({2-[(2,4-dichlorophenyl)amino]-quinazolin-6-yl}oxy)-N-methyl-pyridine-2-carboxamide | 441.3 |
| 39 | 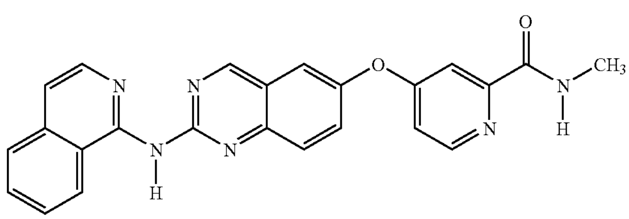 | 4-{[2-(isoquinolin-1-ylamino)-quinazolin-6-yl]oxy}-N-methyl-pyridine-2-carboxamide | 423.4 |
| 40 | 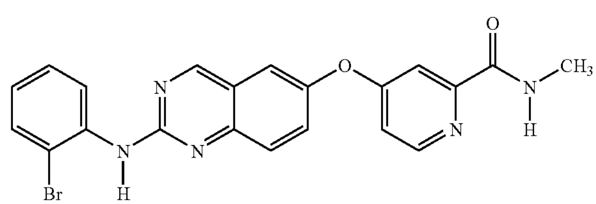 | 4-({2-[(2-bromophenyl)amino]-quinazolin-6-yl}oxy)-N-methyl-pyridine-2-carboxamide | 451.3 |
| 41 | 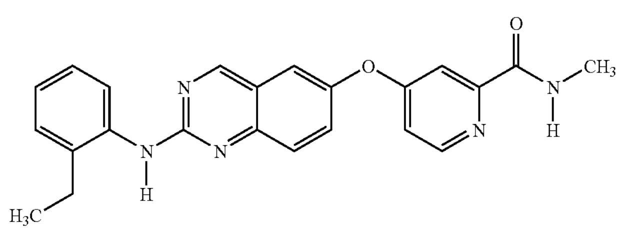 | 4-({2-[(2-ethylphenyl)amino]-quinazolin-6-yl}oxy)-N-methyl-pyridine-2-carboxamide | 400.5 |
| 42 | 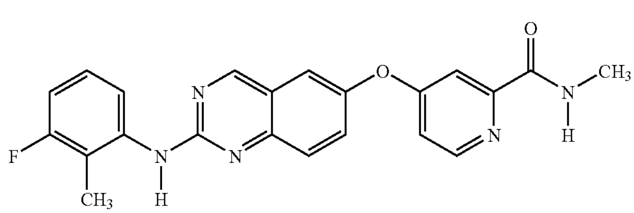 | 4-({2-[(3-fluoro-2-methylphenyl)amino]quinazolin-6-yl}oxy)-N-methylpyridine-2-carboxamide | 404.4 |

TABLE 3-continued

| Example | Structure | Name | MH+ |
|---|---|---|---|
| 43 | 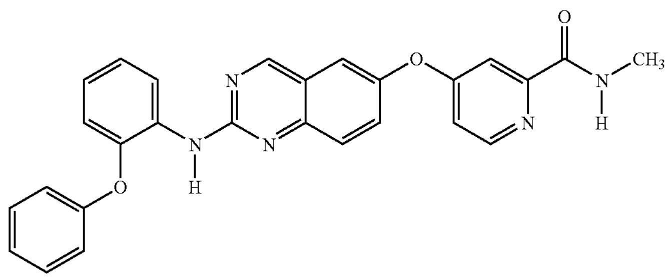 | N-methyl-4-[(2-{[2-(phenyloxy)-phenyl]amino}quinazolin-6-yl)oxy]pyridine-2-carboxamide | 464.5 |
| 44 | 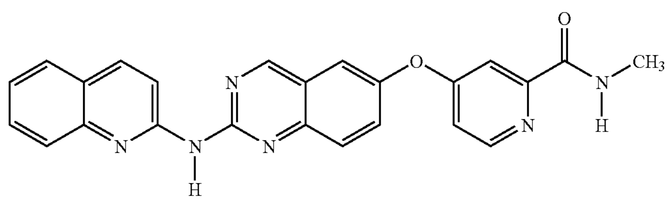 | N-methyl-4-{[2-(quinolin-2-ylamino)quinazolin-6-yl]oxy}-pyridine-2-carboxamide | 423.4 |
| 45 | 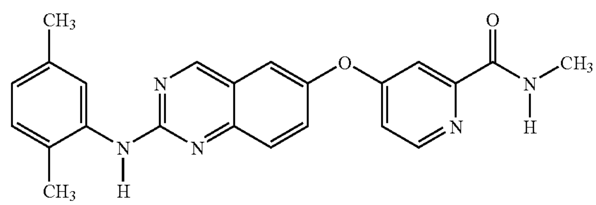 | 4-({2-[(2,5-dimethylphenyl)-amino]quinazolin-6-yl}oxy)-N-methylpyridine-2-carboxamide | 400.5 |
| 46 | 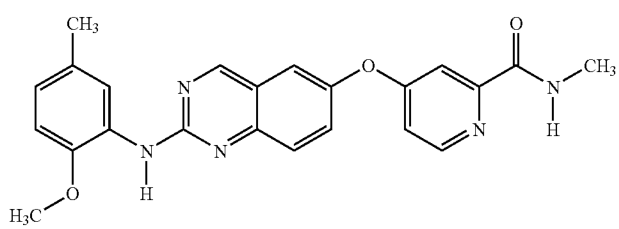 | N-methyl-4-[(2-{[5-methyl-2-(methyloxy)phenyl]amino}-quinazolin-6-yl)oxy]pyridine-2-carboxamide | 416.5 |
| 47 | 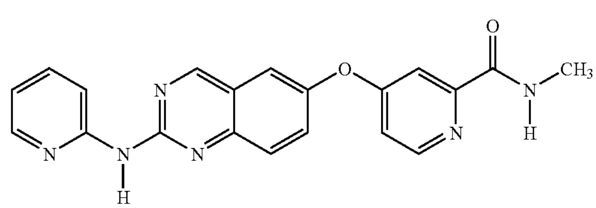 | N-methyl-4-{[2-(pyridin-2-ylamino)quinazolin-6-yl]oxy}-pyridine-2-carboxamide | 373.4 |
| 48 | 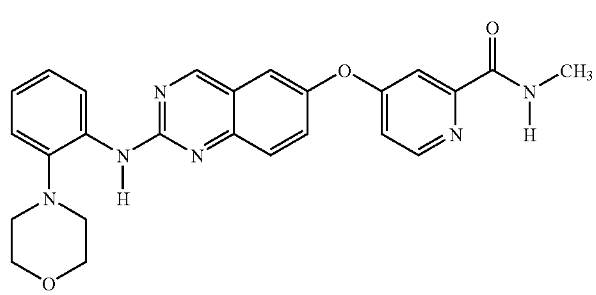 | N-methyl-4-({2-[(2-morpholin-4-ylphenyl)amino]quinazolin-6-yl}oxy)pyridine-2-carboxamide | 457.5 |

TABLE 3-continued

| Example | Structure | Name | MH+ |
|---|---|---|---|
| 49 | 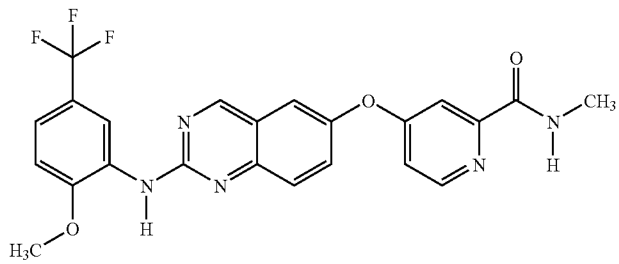 | N-methyl-4-[(2-{[2-(methyloxy)-5-(trifluoromethyl)phenyl]amino}quinazolin-6-yl)oxy]pyridine-2-carboxamide | 470.4 |
| 50 | 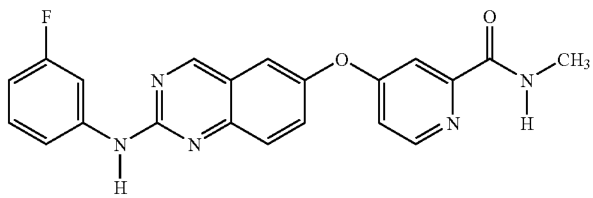 | 4-({2-[(3-fluorophenyl)amino]-quinazolin-6-yl}oxy)-N-methyl-pyridine-2-carboxamide | 390.4 |
| 51 | 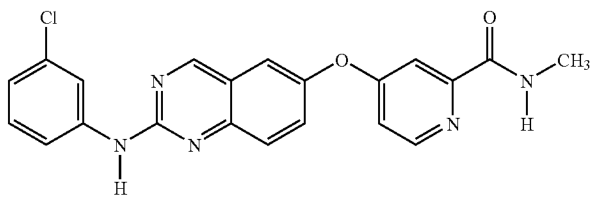 | 4-({2-[(3-chlorophenyl)amino]-quinazolin-6-yl}oxy)-N-methyl-pyridine-2-carboxamide | 406.8 |
| 52 | 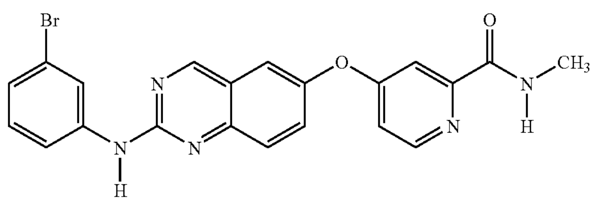 | 4-({2-[(3-bromophenyl)amino]-quinazolin-6-yl}oxy)-N-methyl-pyridine-2-carboxamide | 451.3 |
| 53 | 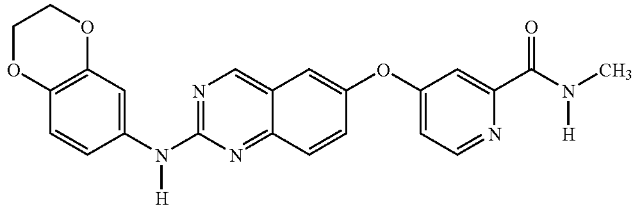 | 4-{[2-(2,3-dihydro-1,4-benzo-dioxin-6-ylamino)quinazolin-6-yl]oxy}-N-methylpyridine-2-carboxamide | 430.4 |
| 54 | 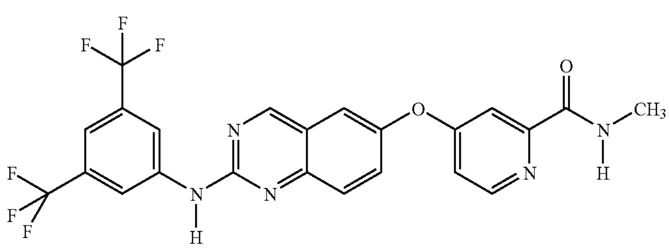 | 4-[(2-{[3,5-bis(trifluoromethyl)-phenyl]amino}quinazolin-6-yl)-oxy]-N-methylpyridine-2-carboxamide | 508.4 |
| 55 | 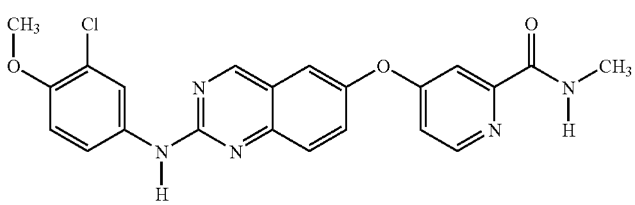 | 4-[(2-{[3-chloro-4-(methyloxy)-phenyl]amino}quinazolin-6-yl)-oxy]-N-methylpyridine-2-carboxamide | 436.9 |

TABLE 3-continued

| Example | Structure | Name | MH+ |
|---|---|---|---|
| 56 | 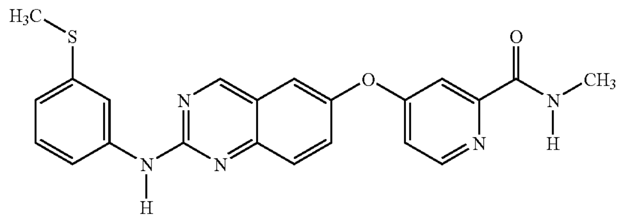 | N-methyl-4-[(2-{[3-(methylthio)-phenyl]amino}quinazolin-6-yl)-oxy]pyridine-2-carboxamide | 418.5 |
| 57 | 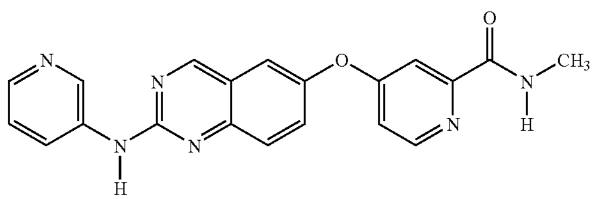 | N-methyl-4-{[2-(pyridin-3-yl-amino)quinazolin-6-yl]oxy}-pyridine-2-carboxamide | 373.4 |
| 58 | 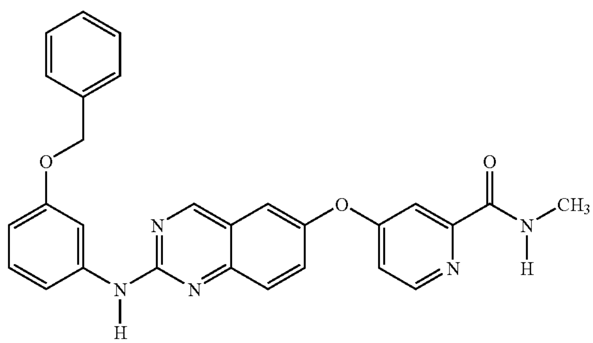 | N-methyl-4-{8 2-({3-[(phenyl-methyl)oxy]phenyl}amino)quinazolin-6-yl]oxy}pyridine-2-carboxamide | 478.5 |
| 59 | 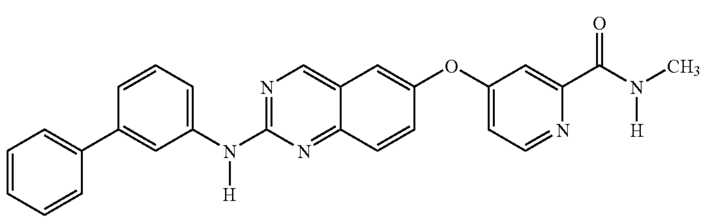 | 4-{[2-(1,1'-biphenyl-3-ylamino)-quinazolin-6-yl]oxy}-N-methyl-pyridine-2-carboxamide | 448.5 |
| 60 | 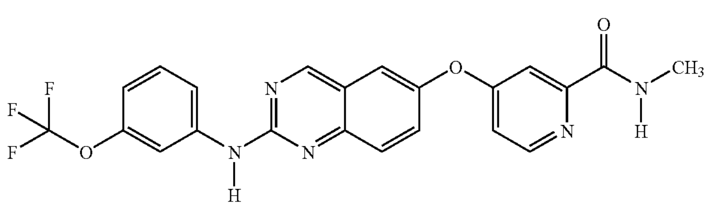 | N-methyl-4-{[2-({3-[(trifluoro-methyl)oxy]phenyl}amino)-quinazolin-6-yl]oxy}pyridine-2-carboxamide | 456.4 |
| 61 | 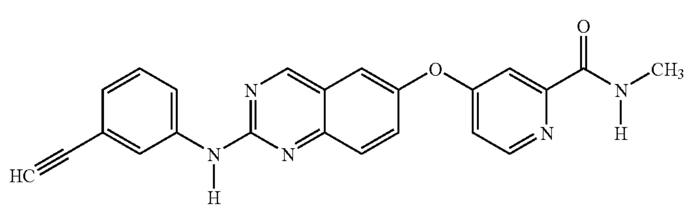 | 4-({2-[(3-ethynylphenyl)amino]-quinazolin-6-yl}oxy)-N-methyl-pyridine-2-carboxamide | 396.4 |

TABLE 3-continued

| Example | Structure | Name | MH+ |
|---|---|---|---|
| 62 | 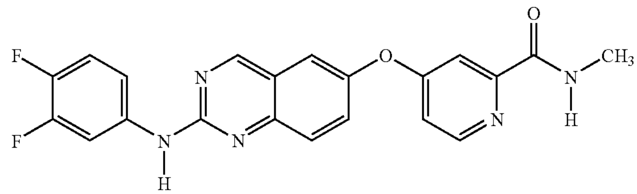 | 4-({2-[(3,4-difluorophenyl)amino]-quinazolin-6-yl}oxy)-N-methyl-pyridine-2-carboxamide | 408.4 |
| 63 | 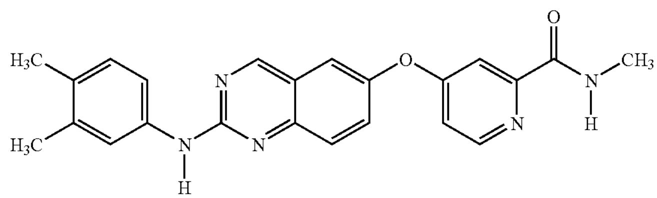 | 4-({2-[(3,4-dimethylphenyl)-amino]quinazolin-6-yl}oxy)-N-methylpyridine-2-carboxamide | 400.5 |
| 64 | 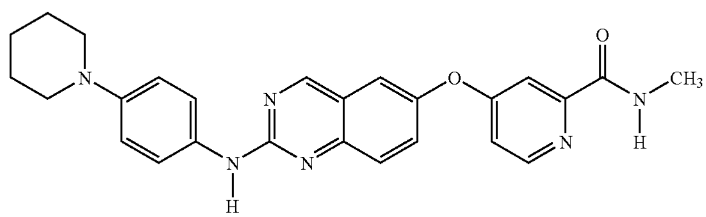 | N-methyl-4-({2-[(4-piperidin-1-ylphenyl)amino]quinazolin-6-yl}-oxy)pyridine-2-carboxamide | 455.5 |
| 65 | 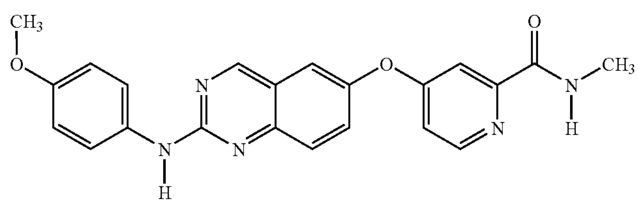 | N-methyl-4-[(2-{[4-(methyloxy)-phenyl]amino}quinazolin-6-yl)-oxy]pyridine-2-carboxamide | 402.4 |
| 66 | 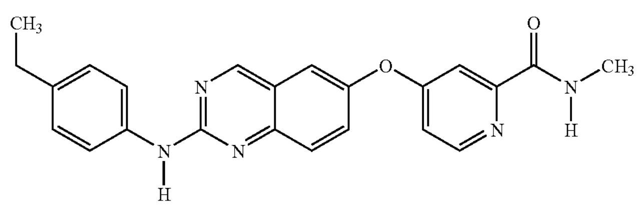 | 4-({2-[(4-ethylphenyl)amino]-quinazolin-6-yl}oxy)-N-methyl-pyridine-2-carboxamide | 400.5 |
| 67 | 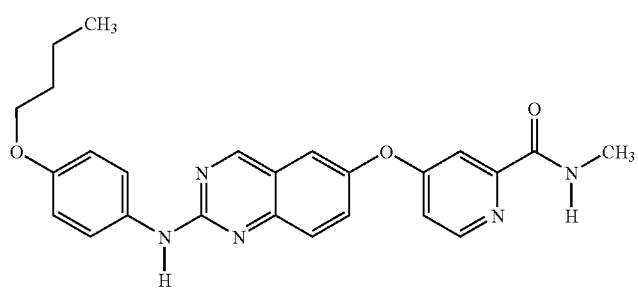 | 4-[(2-{[4-(butyloxy)phenyl]-amino}quinazolin-6-yl)oxy]-N-methylpyridine-2-carboxamide | 444.5 |
| 68 | 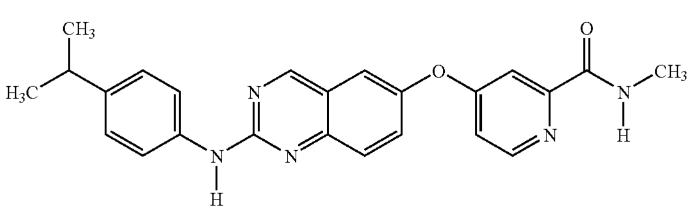 | N-methyl-4-[(2-{[4-(1-methyl-ethyl)phenyl]amino}quinazolin-6-yl)oxy]pyridine-2-carboxamide | 414.5 |

TABLE 3-continued

| Example | Structure | Name | MH+ |
|---|---|---|---|
| 69 | 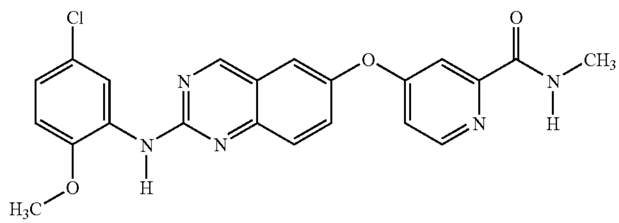 | 4-[(2-{[5-chloro-2-(methyloxy)-phenyl]amino}quinazolin-6-yl)-oxy]-N-methylpyridine-2-carboxamide | 436.9 |
| 70 | 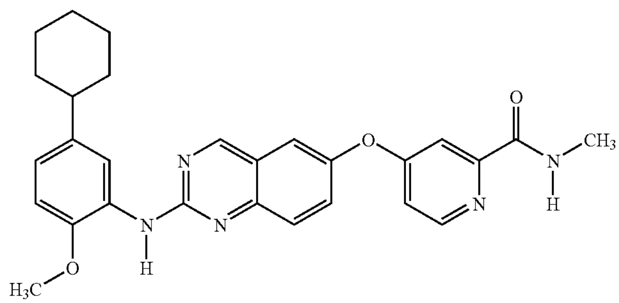 | 4-[(2-{[5-cyclohexyl-2-(methyl-oxy)phenyl]amino}quinazolin-6-yl)oxy]-N-methylpyridine-2-carboxamide | 484.6 |
| 71 | 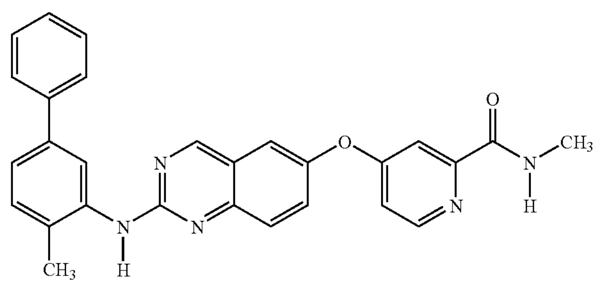 | N-methyl-4-({2-[(4-methyl-1,1'-biphenyl-3-yl)amino]quinazolin-6-yl}oxy)pyridine-2-carboxamide | 462.5 |
| 72 | 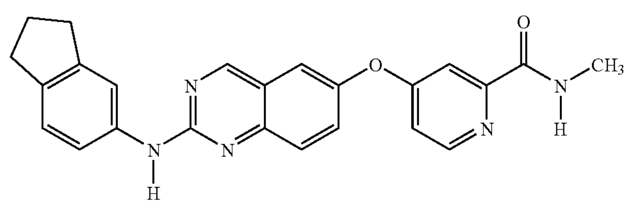 | 4-{[2-(2,3-dihydro-1H-inden-5-ylamino)quinazolin-6-yl]oxy}-N-methylpyridine-2-carboxamide | 412.5 |
| 73 | 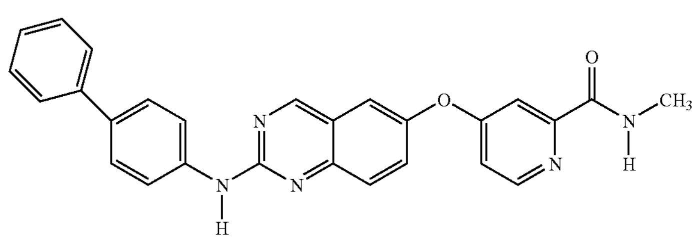 | 4-{[2-(1,1'-biphenyl-4-ylamino)-quinazolin-6-yl]oxy}-N-methyl-pyridine-2-carboxamide | 448.5 |
| 74 | 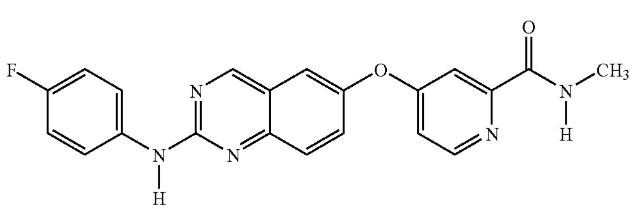 | 4-({2-[(4-fluorophenyl)amino]-quinazolin-6-yl}oxy)-N-methyl-pyridine-2-carboxamide | 390.4 |

TABLE 3-continued

| Example | Structure | Name | MH+ |
|---|---|---|---|
| 75 | 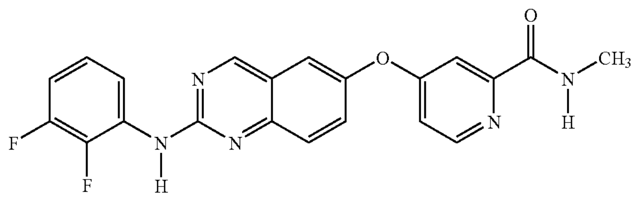 | 4-({2-[(2,3-difluorophenyl)amino]-quinazolin-6-yl}oxy)-N-methyl-pyridine-2-carboxamide | 408.4 |
| 76 | 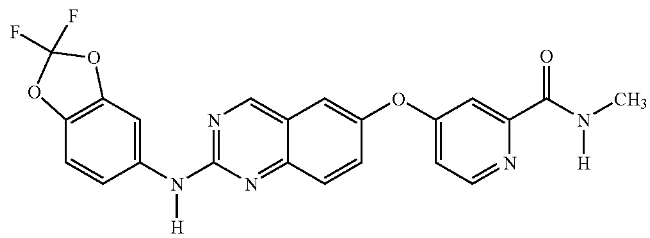 | 4-({2-[(2,2-difluoro-1,3-benzo-dioxol-5-yl)amino]quinazolin-6-yl}oxy)-N-methylpyridine-2-carboxamide | 452.4 |
| 77 | 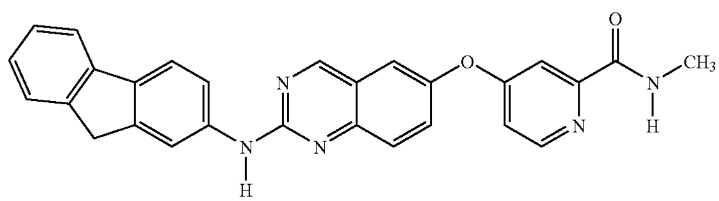 | 4-{[2-(9H-fluoren-2-ylamino)-quinazolin-6-yl]oxy}-N-methyl-pyridine-2-carboxamide | 460.5 |
| 78 | 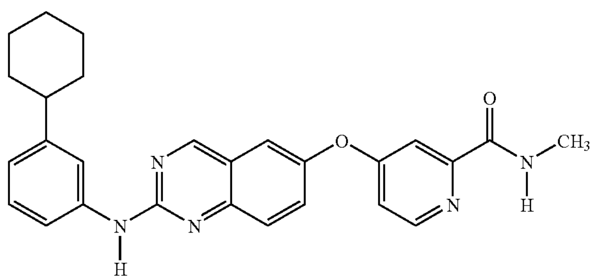 | 4-({2-[(3-cyclohexylphenyl)-amino]quinazolin-6-yl}oxy)-N-methylpyridine-2-carboxamide | 454.5 |
| 79 | 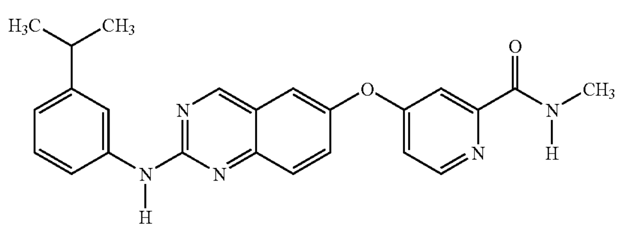 | N-methyl-4-[(2-{[3-(1-methyl-ethyl)phenyl]amino}quinazolin-6-yl)oxy]pyridine-2-carboxamide | 414.5 |
| 80 | 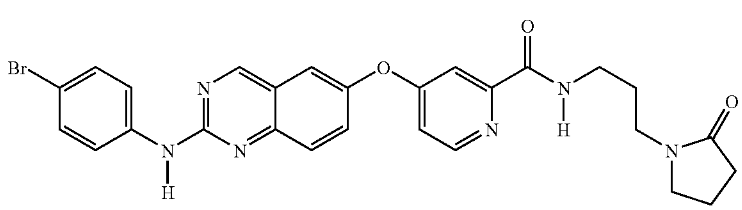 | 4-({2-[(4-bromophenyl)amino]-quinazolin-6-yl}oxy)-N-[3-(2-oxopyrrolidin-1-yl)propyl]-pyridine-2-carboxamide | 562.4 |
| 81 | 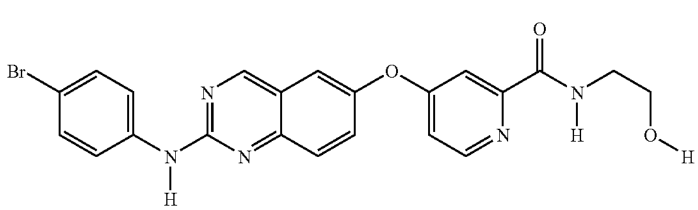 | 4-({2-[(4-bromophenyl)amino]-quinazolin-6-yl}oxy)-N-(2-hydroxyethyl)pyridine-2-carboxamide | 481.3 |

TABLE 3-continued

| Example | Structure | Name | MH+ |
|---|---|---|---|
| 82 | 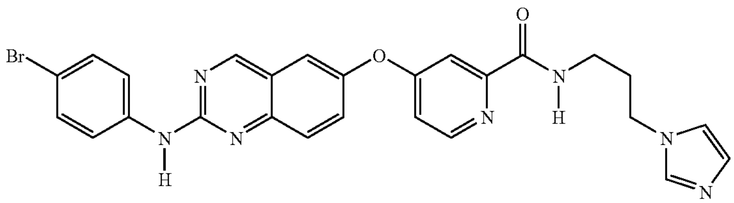 | 4-({2-[(4-bromophenyl)amino]-quinazolin-6-yl}oxy)-N-[3-(1H-imidazol-1-yl)propyl]pyridine-2-carboxamide | 545.4 |
| 83 | 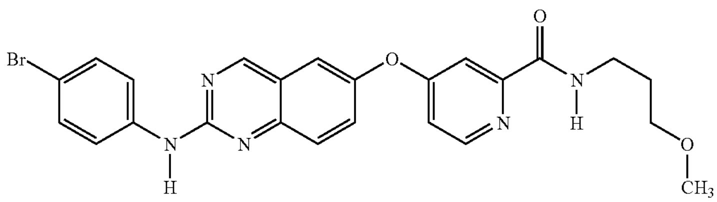 | 4-({2-[(4-bromophenyl)amino]-quinazolin-6-yl}oxy)-N-[3-(methyloxy)propyl]pyridine-2-carboxamide | 509.4 |
| 84 | 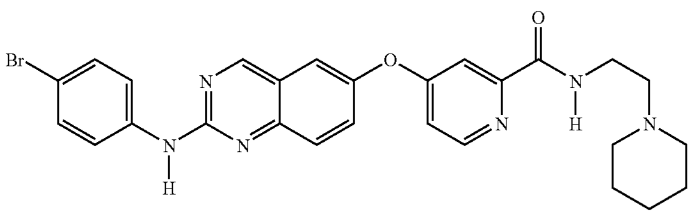 | 4-({2-[(4-bromophenyl)amino]-quinazolin-6-yl}oxy)-N-(2-piperidin-1-ylethyl)pyridine-2-carboxamide | 548.5 |
| 85 | 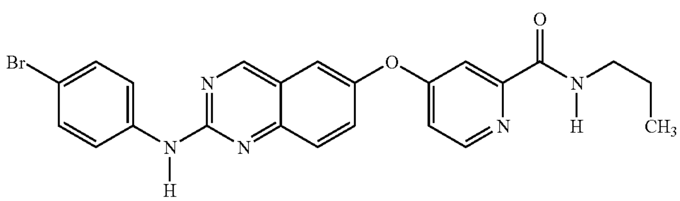 | 4-({2-[(4-bromophenyl)amino]-quinazolin-6-yl}oxy)-N-propyl-pyridine-2-carboxamide | 479.3 |
| 86 | 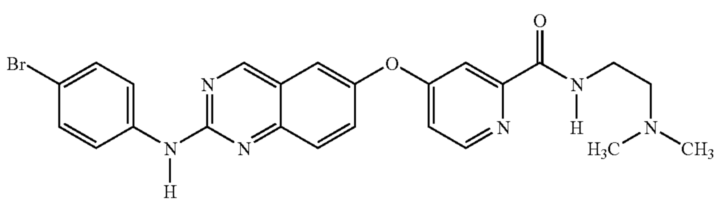 | 4-({2-[(4-bromophenyl)amino]-quinazolin-6-yl}oxy)-N-[2-(dimethylamino)ethyl]pyridine-2-carboxamide | 508.4 |
| 87 | 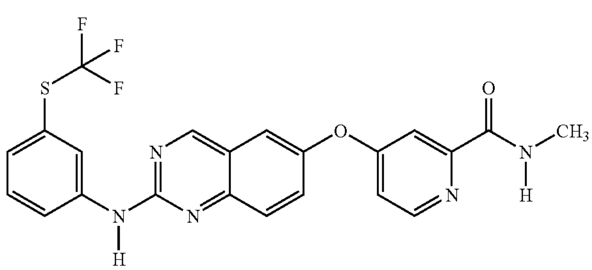 | N-methyl-4-{[2-({3-[(trifluoromethyl)thio]phenyl}amino)-quinazolin-6-yl]oxy}pyridine-2-carboxamide | 472.5 |
| 88 | 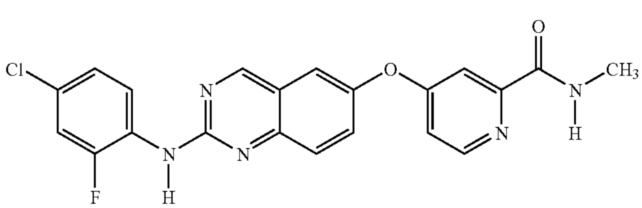 | 4-({2-[(4-chloro-2-fluorophenyl)-amino]quinazolin-6-yl}oxy)-N-methylpyridine-2-carboxamide | 424.8 |

TABLE 3-continued

| Example | Structure | Name | MH+ |
|---|---|---|---|
| 89 | 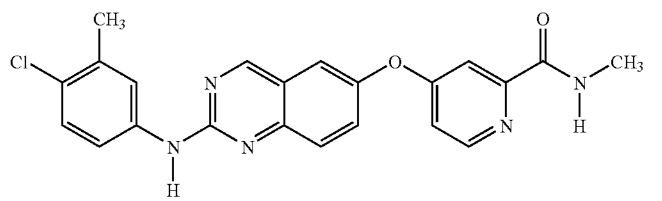 | 4-({2-[(4-chloro-3-methylphenyl)-amino]quinazolin-6-yl}oxy)-N-methylpyridine-2-carboxamide | 420.9 |
| 90 | 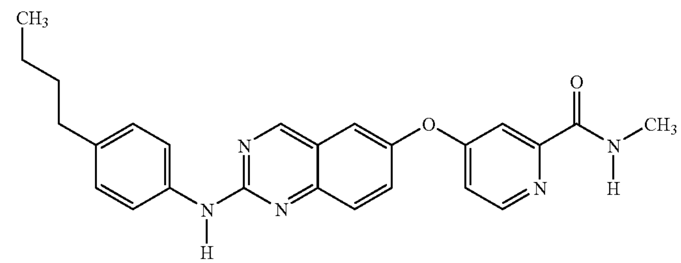 | 4-({2-[(4-butylphenyl)amino]-quinazolin-6-yl}oxy)-N-methyl-pyridine-2-carboxamide | 428.5 |

Example 91

Synthesis of (4-{2-[(4-bromo-3-methylphenyl)amino](6-quinolyloxy)}-(2-pyridyl))-N-methylcarboxamide

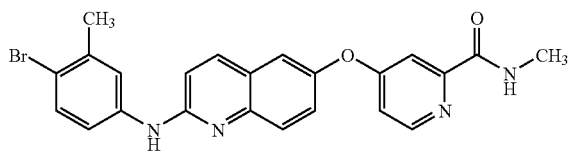

Step 1. Synthesis of 2-chloroquinolin-6-ol

A solution of quinoline2,6-diol (1 eq) in THF (0.25 M) was treated with POCl$_3$ (1.1 eq) and a drop of DMF. Crushed ice was added to the reaction mixture and EtOAc was added and neutralized with a solution of sodium bicarbonate. The mixture was brought back to pH 6-7 with 1N HCl and ethyl acetate layer was separated, washed with water and brine to provide title compound.

MS: MH$^+$=180.6

Step 2. Synthesis of 2-[(4-bromo-3-methylphenyl)amino]quinolin-6-ol

The mixture containing 2-chloroquinolin-6-ol (1eq), 4-bromo3-methylaniline (2 eq) and diisopropylethylamine in ethanol (1 M) was refluxed overnight. The resultant mixture was concentrated and purified on silica gel to provide the desired product. The mixture containing 2-chloroquinolin-6-ol (1 eq), 4-bromo3-methylaniline (2 eq) and diisopropylethylamine in ethanol (1M) was refluxed overnight. The resultant mixture was concentrated and purified on silica gel to provide the desired product.

MS: MH$^+$=329.1

Step 3. Synthesis of (4-{2-[(4-bromo-3-methylphenyl)amino](6-quinolyloxy)}(2-pyridyl))-N-methylcarboxamide The mixture of 2-[(4-bromo-3-methylphenyl)amino]quinolin-6-ol and potassium bis(trimethylsilyl)amide (2 eq), was stirred in dimethylformamide for 30 min at room temperature. To this mixture was added (4-chloro(2-pyridyl)-N-methylcarboxamide (1 eq) and potassium carbonate (1.2 eq) and microwaved for 6 mins at 170° C. The reaction mixture was then concentrated and partitioned between ethyl acetate and water. The organic layer was separated and washed with brine, dried, filtered and concentrated. Purification on Prep LC yielded the desired product.

MS: MH$^+$=463.3

Example 92

Synthesis of N-methyl-4-[(2-{[3-(1-methylethyl)phenyl]amino}quinolin-6-yl)oxy]pyridine-2-carboxamide

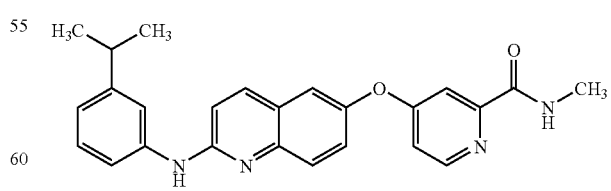

Following the procedure of Example 91, N-methyl-4-[(2-{[3-(1-methylethyl)-phenyl]amino}quinolin-6-yl)oxy]pyridine-2-carboxamide was synthesized.

MS: MH$^+$=413.5

Example 93

Synthesis of 4-[2-(3-tert-Butyl-phenylamino)-quinoxalin-6-yloxy]-pyridine-2-carboxylic Acid Methylamide

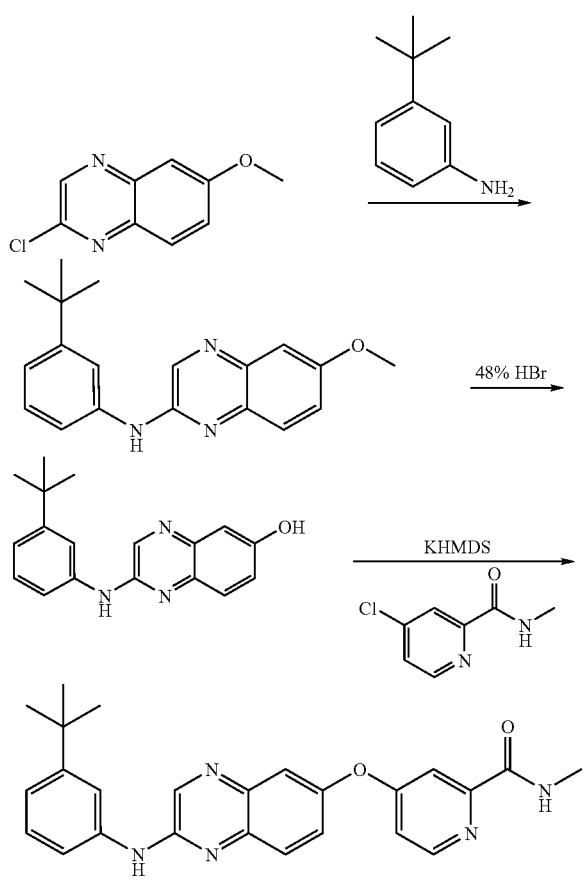

1. Synthesis of (3-tert-Butyl-phenyl)-(6-methoxy-quinoxalin-2-yl)-amine

A solution containing 2-chloro-6-methoxyquinoxaline (synthesized as described in *J. Chem. Soc.* Perkin Trans 2001, 978-984) (1 eq), 3-t-butylaniline (2 eq) in ethanol was heated at 80° C. overnight. The resultant mixture was concentrated and partitioned between ethyl acetate and water. The organic layer was washed with brine and dried. Purification on silica gel gave the desired product.
MS: MH$^+$=308.3

2. Synthesis of 2-(3-tert-Butyl-phenylamino)-quinoxalin-6-ol

The mixture of (3-tert-Butyl-phenyl)-(6-methoxy-quinoxalin-2-yl)-amine and hydrobromic acid (48%) was subjected to the microwave at 140° C. for 6 mins. to yield the desired product. The mixture was neutralized with sodium bicarbonate solution and taken in ethyl acetate. The organic layer was washed with water and brine, concentrated, and purified on silica gel.
MS: MH$^+$=294.3

3. Synthesis of 4-[2-(3-tert-Butyl-phenylamino)-quinoxalin-6-yloxy]-pyridine-2-carboxylic Acid Methylamide The mixture containing 2-(3-tert-butyl-phenylamino)-quinoxalin-6-ol (1 eq), potassiumbis(trimethylsilyl)amide (4eq), was stirred in dimethylformamide for 30 min. at room temperature. To this mixture was added 4-chloro-pyridine-2-carboxylic acid methylamide (1 eq) and potassium carbonate (1.2 eq) and microwaved for 6 mins. at 170° C. The reaction mixture was then concentrated and partitioned between ethyl acetate and water. The organic layer was separated and washed with brine, dried, filtered and concentrated. Purification on Prep LC yielded the desired product.
MS: MH$^+$=428.5

Example 94

Raf/Mek Filtration Assay

Buffers
  Assay buffer: 50 mM Tris, pH 7.5, 15 mM MgCl$_2$, 0.1 mM EDTA, 1 mM DTT
  Wash buffer: 25 mM Hepes, pH 7.4, 50 mM sodium pyrophosphate, 500 mM NaCl
  Stop reagent: 30 mM EDTA Materials
  Raf, active: Upstate Biotech #14-352
  Mek, inactive: Upstate Biotech #14-205
  $^{33}$P-ATP: NEN Perkin Elmer #NEG 602 h
  96 well assay plates: Falcon U-bottom polypropylene plates #35-1190
  Filter apparatus: Millipore #MAVM 096OR
  96 well filtration plates: Millipore Immobilon 1 #MAIP NOB
  Scintillation fluid: Wallac OptiPhase "SuperMix" #1200-439

Assay Conditions
  Raf approximately 120 pM
  Mek approximately 60 nM
  $^{33}$P-ATP 100 nM
  Reaction time 45-60 minutes at room temperature Assay Protocol
  Raf and Mek were combined at 2× final concentrations in assay buffer (50 mM Tris, pH 7.5, 15 mM MgCl$_2$. 0.1 mM EDTA and 1 mM DTT) and dispensed 15 µl per well in polypropylene assay plates (Falcon U-bottom polypropylene 96 well assay plates #35-1190. Background levels are determined in wells containing Mek and DMSO without Raf.
  To the Raf/Mek containing wells was added 3 µl of 10× of a raf kinase inhibitor test compound diluted in 100% DMSO. The raf kinase activity reaction was started by the addition of 12 µl per well of 2.5× $^{33}$P-ATP diluted in assay buffer. After 45-60 minutes, the reactions were stopped with the addition of 70 µl of stop reagent (30 mM EDTA). Filtration plates were pre-wetted for 5 min with 70% ethanol, and then rinsed by filtration with wash buffer. Samples (90 µl) from the reaction wells were then transferred to the filtration plates. The filtration plates were washed 6× with wash buffer using Millipore filtration apparatus. The plates were dried and 100 µl per well of scintillation fluid (Wallac OptiPhase "SuperMix" #1200-439) was added. The CPM is then determined using a Wallac Microbeta 1450 reader.

Example 95

Assay 2: Biotinylated Raf Screen

In Vitro Raf Screen

The activity of various isoforms of Raf serine/threonine kinases can be measured by providing ATP, MEK substrate, and assaying the transfer of phosphate moiety to the MEK residue. Recombinant isoforms of Raf were obtained by purification from sf9 insect cells infected with a human Raf recombinant baculovirus expression vector. Recombinant kinase inactive MEK was expressed in E. coli and labeled with Biotin post purification. For each assay, test compounds were serially diluted in DMSO then mixed with Raf (0.50 nM) and kinase inactive biotin-MEK (50 nM) in reaction buffer plus ATP (1 μM). Reactions were subsequently incubated for 2 hours at room temperature and stopped by the addition of 0.5 M EDTA. Stopped reaction mixture was transferred to a neutradavin-coated plate (Pierce) and incubated for 1 hour. Phosphorylated product was measured with the DELFIA time-resolved fluorescence system (Wallac), using a rabbit anti-p-MEK (Cell Signaling) as the primary antibody and europium, labeled anti-rabbit as the secondary antibody. Time resolved fluorescence was read on a Wallac 1232 DELFIA fluorometer. The concentration of each compound for 50% inhibition ($IC_{50}$) was calculated by non-linear regression using XL Fit data analysis software.

Using the procedures of Examples 94 or 95, the compounds of Examples 1-93 were shown to have a raf kinase inhibitory activity at an $IC_{50}$ of less than 5 μM.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A compound of the formula (IV):

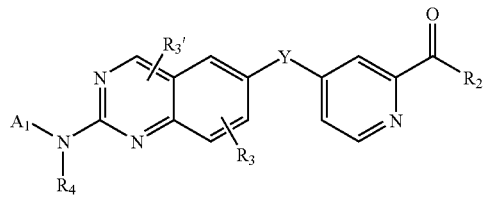

wherein,
Y is O or S;
$A_1$ is substituted or unsubstituted alkyl, cycloalkyl, heterocycloalkyl, aryl, polycyclic aryl, polycyclic arylalkyl, heteroaryl, biaryl, heteroarylaryl, heteroarylheteroaryl, cycloalkylalkyl, cycloalkylaryl, heterocycloalkyl, heterocycloalkylalkyl, heterocycloaryl, arylalkyl, heteroarylalkyl, biarylalkyl, or heteroarylarylalkyl;
$R_2$ is $NR_6R_7$ or hydroxyl;
$R_3$ and $R_{3'}$ are independently selected from hydrogen, halogen, loweralkyl, or loweralkoxy;
$R_4$ is hydrogen, hydroxyl or substituted or unsubstituted alkyl; and
$R_6$ and $R_7$ are independently selected from hydrogen, and substituted or unsubstituted alkyl, alkoxy, alkoxyalkyl, aminoalkyl, amidoalkyl, acyl, cycloalkyl, heterocycloalkyl, aryl, heteroaryl, alkyloxyalkylheterocyclo, and heteroarylalkyl; or $R_6$ and $R_7$ are taken together to form substituted or unsubstituted heterocyclo or heteroaryl; or a stereoisomer, tautomer, prodrug or pharmaceutically acceptable salt thereof.

2. A compound of claim 1 wherein Y is O.

3. A compound of claim 1 wherein $A_1$ is selected from the group consisting of substituted or unsubstituted phenyl, phenylalkyl, pyridyl, pyrimidinyl, pyridylalkyl, pyrimidinylalkyl, alkylbenzoate, thiophene, thiophene-2-carboxylate, indenyl, 2,3-dihydroindenyl, tetralinyl, trifluorophenyl, (trifluoromethyl)thiophenyl, morpholinyl, N-piperazinyl, N-morpholinylalkyl, piperazinylalkyl, cyclohexylalkyl, indolyl, 2,3-dihydroindolyl, 1-aceytl-2,3-dihydroindolyl, cycloheptyl, bicyclo[2.2.1]hept-2-yl, pyrrolidinyl, pyrrolidin-1-yl, pyrrolidin-1-ylalkyl, 4-amino(imino)methylphenyl, isoxazolyl, indazolyl, adamantyl, bicyclohexyl, quinuclidinyl, imidazolyl, benzimidazolyl, imidazolylphenyl, phenylimidazolyl, pthalamido, napthyl, naphthalenyl, benzophenone, anilinyl, anisolyl, quinolinyl, quinolinonyl, phenylsulfonyl, phenylalkylsulfonyl, 9H-flouren-1-yl, piperidin-1-yl, piperidin-1-ylalkyl, cyclopropyl, cyclopropylalkyl, furanyl, N-methylpiperidin-4-yl, pyrrolidin-4-ylpyridinyl, 4-diazepan-1-yl, hydroxypyrrolidn-1-yl, dialkylaminopyrrolidin-1-yl, and 1,4'-bipiperidin-1'-yl.

4. A compound of claim 1 wherein $A_1$ is substituted or unsubstituted phenyl.

5. A compound of claim 4 wherein $A_1$ is substituted phenyl selected from the group consisting of substituted or unsubstituted hydroxyphenyl, hydroxyalkylphenyl, alkylphenyl, dialkylphenyl, trialkylphenyl, alkoxyphenyl, dialkoxyphenyl, alkoxyalkylphenyl, halophenyl, dihalophenyl, halo alkylphenyl, haloalkoxyphenyl, alkylbalophenyl, alkoxyhalophenyl, alkylthiophenyl, aminophenyl, nitrophenyl, acetylphenyl, sulfamoylphenyl, biphenyl, alkoxybiphenyl, cyclohexylphenyl, phenyloxyphenyl, dialkylaminophenyl, morpholinylphenyl, heterocyclylcarbonylphenyl, heterocyclylphenyl, heterocyclylalkylphenyl, furanylphenyl, (1,4'-bipiperidin-1'-ylcarbonyl)phenyl, pyrimidin-5-ylphenyl, and quinolidinylphenyl.

6. A compound of claim 5 wherein $A_1$ is substituted phenyl selected from the group consisting of chlorophenyl, fluorophenyl, bromophenyl, iodophenyl, dichlorophenyl, difluorophenyl, dibromophenyl, fluorochlorophenyl, bromochlorophenyl, trifluoromethylphenyl, trifluoromethoxyphenyl, alkylbromophenyl, trifluoromethylbromophenyl, alkylchlorophenyl, trifluoromethylchlorophenyl, alkylfluorophenyl, and trifluoromethylfluorophenyl.

7. A compound of claim 1 wherein $R_2$ is $NR_6R_7$, $R_6$ is hydrogen and $R_7$ is selected from hydrogen, and substituted or unsubstituted alkyl, alkoxy, alkoxyalkyl, aminoalkyl, amidoalkyl, acyl, cycloalkyl, heterocycloalkyl, aryl, heteroaryl, alkyloxyalkylheterocyclo, and heteroarylalkyl.

8. A compound of claim 1 wherein $R_3$ is loweralkoxy.

9. A compound of claim 8 wherein $R_3$ is methoxy.

10. A compound of claim 1 wherein $R_4$ is hydrogen.

11. A compound of claim 1 wherein $R_4$ is loweralkyl.

12. A compound of claim 11 wherein $R_4$ is methyl.

13. A compound of claim 1 having the formula:

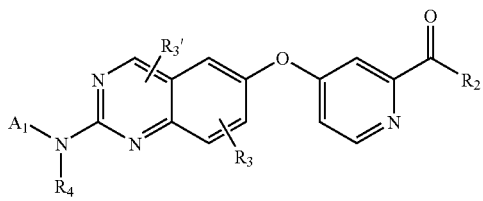

or a stereoisomer, tautomer, prodrug or pharmaceutically acceptable salt thereof.

14. A compound of claim 1 wherein $R_2$ is $NR_6R_7$, $R_6$ is H, and $R_7$ is methyl.

15. A composition comprising an amount of a compound of claim 1 or 13 effective to inhibit Raf activity in a human or animal subject when administered thereto, together with a pharmaceutically acceptable carrier.

16. A composition of claim 15 which further comprises at least one additional agent for the treatment of cancer.

17. A composition of claim 16 in which the at least one additional agent for the treatment of cancer is selected from irinotecan, topotecan, gemcitabine, 5-fluorouracil, leucovorin carboplatin, cisplatin, taxanes, tezacitabine, cyclophosphamide, vinca alkaloids, imatinib, anthracyclines, rituximab, trastuzumab, dacarbazine, aldesleukin, capecitabine, and Iressa (gefitinib).

* * * * *